US012809005B2

(12) United States Patent
McCaw et al.

(10) Patent No.: US 12,809,005 B2
(45) Date of Patent: Nov. 24, 2026

(54) SYSTEMS AND METHODS FOR ELASTOGRAPHIC AND VISCOELASTOGRAPHIC IMAGING

(71) Applicant: Elastance Imaging LLC, Columbus, OH (US)

(72) Inventors: Kenneth J. McCaw, Westerville, OH (US); William D. Timmons, Columbus, OH (US)

(73) Assignee: Elastance Imaging, LLC, Columbus, OH (US)

( * ) Notice: Subject to any disclaimer, the term of this patent is extended or adjusted under 35 U.S.C. 154(b) by 811 days.

(21) Appl. No.: 17/040,824

(22) PCT Filed: Mar. 25, 2019

(86) PCT No.: PCT/US2019/023944
§ 371 (c)(1),
(2) Date: Sep. 23, 2020

(87) PCT Pub. No.: WO2019/191009
PCT Pub. Date: Oct. 3, 2019

(65) Prior Publication Data

US 2021/0018606 A1 Jan. 21, 2021

Related U.S. Application Data

(60) Provisional application No. 62/716,303, filed on Aug. 8, 2018, provisional application No. 62/647,672, filed on Mar. 24, 2018.

(51) Int. Cl.

| | |
|---|---|
| ***G01S 7/52*** | (2006.01) |
| ***A61B 8/00*** | (2006.01) |
| ***B06B 1/02*** | (2006.01) |

(52) U.S. Cl.
CPC ........ *G01S 7/52042* (2013.01); *B06B 1/0246* (2013.01); *G01S 7/52071* (2013.01); *A61B 8/485* (2013.01)

(58) Field of Classification Search
USPC .............................................................. 367/7
See application file for complete search history.

(56) References Cited

U.S. PATENT DOCUMENTS

| | | | |
|---|---|---|---|
| 8,267,865 | B2 | 9/2012 | Hoyt et al. |
| 8,602,994 | B2 | 12/2013 | Zheng et al. |

(Continued)

OTHER PUBLICATIONS

Tzschatzsch et al. ("multifrequency time-harmonic elastography for the measurement of liver viscoelasticity in large tissue windows", ultrasound in Med. 2014) (Year: 2014).*

(Continued)

*Primary Examiner* — Michael J Carey
*Assistant Examiner* — Marjan Saboktakin
(74) *Attorney, Agent, or Firm* — Jenei LLC

(57) ABSTRACT

A High Definition ViscoElastography (HDVE) inertial driver apparatus of an imaging system and method includes one or more HDVE inertial driver devices. Each HDVE inertial driver device has: (i) a driver interface that enables receiving a driver signal from a controller; (ii) a resonating surface; and (iii) an inertial driver communicatively coupled to the driver interface and mechanically coupled to the resonating surface to independently generate a resonating displacement of the resonating surface. A support member of the HDVE inertial driver apparatus positions the two or more HDVE inertial driver devices into acoustic contact with a body to produce a shear wave field through a volume of tissue within the body or a material within an object.

20 Claims, 18 Drawing Sheets

(56) References Cited

U.S. PATENT DOCUMENTS

| | | | | |
|---|---|---|---|---|
| 9,622,711 | B2 | 4/2017 | Zhao et al. | |
| 10,779,799 | B2 | 9/2020 | Chen et al. | |
| 11,510,652 | B2 | 11/2022 | Salcudean et al. | |
| 2005/0251042 | A1 * | 11/2005 | Sandrin | A61B 8/0825 600/443 |
| 2008/0200805 | A1 | 8/2008 | Hoyt et al. | |
| 2012/0271294 | A1 * | 10/2012 | Barthe | A61B 8/4444 606/28 |
| 2014/0316267 | A1 | 10/2014 | Barry et al. | |
| 2014/0350399 | A1 | 11/2014 | Sack et al. | |
| 2015/0099971 | A1 | 4/2015 | Sandrin et al. | |
| 2016/0157035 | A1 * | 6/2016 | Russell | H04R 29/003 381/405 |
| 2019/0192119 | A1 * | 6/2019 | Salcudean | A61B 8/08 |
| 2020/0054217 | A1 * | 2/2020 | Parker | A61B 8/085 |

OTHER PUBLICATIONS

Zhao et al. External vibration multi-directional ultrasound shearwave elastography (EVMUSE): application in liver fibrosis staging. IEEE Trans Med Imaging. Nov. 2014;33(11):2140-8. doi: 10.1109/TMI.2014.2332542. Epub Jul. 9, 2014. PMID: 25020066; PMCID: PMC4216646.

Ormachea et al., Shear Wave Speed Estimation Using Reverberant Shear Wave Fields: Implementation and Feasibility Studies. Ultrasound Med Biol. May 2018;44(5):963-977. doi: 10.1016/j.ultrasmedbio.2018.01.011. Epub Feb. 21, 2018. PMID: 29477745.

Hoyt K, Castaneda B, Zhang M, Nigwekar P, di Sant'agnese PA, Joseph JV, Strang J, Rubens DJ, Parker KJ. Tissue elasticity properties as biomarkers for prostate cancer. Cancer Biomark. 2008;4(4-5):213-25. doi: 10.3233/cbm-2008-44-505. PMID: 18957712; PMCID: PMC3144495.

An L, Mills B, Hah Z, et al. Crawling wave detection of prostate cancer: preliminary in vitro results. Medical Physics. May 2011; 38(5):2563-2571. DOI: 10.1118/1.3569578. PMID: 21776792; PMCID: PMC3104722.

Castaneda B., Hoyt, K., Westesson, K., An, L., Yao, J., Baxter, L., Joseph, J., Strang, J., Rubens, D., & Parker, K. (2009). Performance of three-dimensional sonoelastography in prostate cancer detection: A comparison between ex vivo and in vivo experiments. In 2009 IEEE International Ultrasonics Symposium and Short Courses, IUS 2009 (pp. 519-522). Article 5441763 (Proceedings—IEEE Ultrasonics Symposium). Institute of Electrical and Electronics Engineers Inc.. https://doi.org/10.1109/ULTSYM.2009.5441763.

Hudert et al. (2018), "US Time-Harmonic Elastography: Detection of Liver Fibrosis in Adolescents with Extreme Obesity with Non-alcoholic Fatty Liver Disease", Radiology vol. 288, No. 1 (https://doi.org/10.1148/radiol.2018172928).

Tzschatzsch et al. (2015), "Multifrequency time-harmonic elastography for the measurement of liver viscoelasticity in large tissue windows." Ultrasound Med Biol. Mar. 2015;41(3):724-33. doi: 10.1016/j.ultrasmedbio.2014.11.009. Epub Jan. 28, 2015.

* cited by examiner

SYSTEMS AND METHODS FOR ELASTOGRAPHIC AND VISCOELASTOGRAPHIC IMAGING

CLAIM OF PRIORITY UNDER 35 U.S.C. § 119

The present application for patent claims priority to U.S. Provisional Application No. 62/647,672 entitled "SYSTEMS AND METHODS FOR ELASTOGRAPHIC AND VISCOELASTOGRAPHIC IMAGING" filed Mar. 24, 2018, and U.S. Provisional Application No. 62/716,303 entitled "SYSTEMS AND METHODS FOR ELASTOGRAPHIC AND VISCOELASTOGRAPHIC IMAGING" filed Aug. 8, 2018, which are assigned to the assignee hereof and hereby expressly incorporated by reference herein.

FIELD OF THE INVENTION

The invention relates to elastography and viscoelastography devices and to elastography and viscoelastography methods employing external vibrations. The invention relates to elastography and viscoelastography methods including for imaging, nondestructive testing and seismic mapping.

BACKGROUND OF THE INVENTION

Elastography imaging provides stiffness maps of a tissue or object, wherein the stiffness values are overlaid on an image obtained from a common imaging system such as but not limited to ultrasound and magnetic resonance imaging. The stiffness maps are typically obtained by imaging the tissue or object using an imaging or sensing modality that can monitor the propagation of acoustic vibrations that have been injected into or induced in the tissue or object. The vibrations can be induced using ultrasound generated pushes.

Acoustic Radiation Force Impulse (ARFI) is an elastography technique that uses the ultrasound transducer array itself to produce an acoustic impulse in the tissue or object, in a region of interest. The ultrasound array is then used to monitor the propagation of the resulting tissue displacement along the beam direction and/or the propagation of the induced lateral shear waves. The acoustic impulse must be limited to intensities that are safe (that will not overheat the tissue or object) and that will not overheat the transducer. As a result, ARFI systems typically only penetrate up to 6 cm into the tissue or object, limiting their utility to imaging near surface tissues and objects only. In addition, the ARFI impulse itself creates significant echoes and distortions within the first 1.5 to 2 cm of the ARFI probe's tissue contact point, leading to significant noise within this surface zone within the ARFI-generated elastography images. Low resolution of the ARFI approach limits the efficacy of this technique.

Other forms of elastography, such as Crawling Waves and earlier sonoelastography systems, also use acoustic vibration to induce shear waves into the body or object, typically using external, sometimes multiple, acoustic vibration sources. Crawling waves, for example, use two vibration sources vibrating at slightly different frequencies to induce shear waves into a body or object in such a way as to create interference patterns that slowly move across the field of view. The slowly moving patterns can then be used to measure shear wave length in a region of interest. Unlike ARFI, the external acoustic vibrations and their resulting shear waves safely penetrate deep into the body or object, so the full penetration depth of the ultrasound imaging modality can be used.

In another approach, German Group's has used a loud speaker bolted to bottom of exam table, with holes drilled into the exam table to let the sound waves through, where the sound waves then convert to shear waves propagating through the body. Since the sound waves propagate through the air, potential loudness presents a problem to staff, patients and others. The sound waves are not sealed to the patient skin and noise dampening is not fully covering all escape routes for the sound. Also, air coupling to the patient's body may produce only weak shear waves, especially at higher frequencies, since air is a terrible power transfer media.

Older versions of vibration devices and systems are described such that "high frequency" was considered to be 200 Hz and speculated that such frequencies may not work because of high tissue attenuation at those frequencies.

Reverberant Shear Wave elastography is a method whereby a plurality of acoustic vibration transducers inject vibratory waves of various specific frequencies, phases, and amplitudes from a plurality of directions to create a reverberant shear wave field that can be monitored in a region of interest and used to estimate propagation speed as a function of shear wave frequency, which then can be converted to stiffness as a function of frequency, which in turn can be used to calculate viscosity. The acoustic vibrations and their resulting shear waves safely penetrate deep into the body or object, thereby allowing an ultrasound imaging system to utilize its full depth of imaging. Generally-known reverberant shear wave elastography has similar limitations of early tactile vibration sources, being designed for low frequencies that could not penetrate deeply at the higher frequencies.

For example, EchoSens external vibration system is limited to low frequencies, and has potential aliasing if used at high frequencies (e.g., 4 kHz) in liver because there is not enough time for the round trip ultrasound echo to come back from the liver to sample above the required sample rate dictated by the Shannon Sampling Theorem.

SUMMARY OF THE INVENTION

The present disclosure provides for a device and system for inducing mechanical vibrations in a body or object for elastography and viscoelastography imaging using external vibration, devices for elastography and viscoelastography imaging methods, in which the resulting shear waves have a single frequency, two frequencies, or multiple frequencies (including an infinite number of frequencies such as in band limited white noise), with the ability to provide a range of vibrations below 200 Hz (as used in current elastography systems), while also having the ability to exceed 200 Hz while penetrating deeply into the body or object. In one or more embodiments, the waves comprise at least 2, 3, 4, 5, 6, 7, 8, 9, 10, 12, 14, 15, 20, 25 or more discrete frequencies.

In accordance with one aspect of the present disclosure, a method for measuring a mechanical property of an object using an ultrasound system having a transducer is provided. The method includes providing systems that include an acoustic energy source such as an electro-mechanical vibration driver source or sources that can generate and inject single, multiple, and arbitrary waveforms such as one with a plurality of sinusoids, triangle waves, square waves, complex waves (including noise) of a single frequency or of various frequencies, phases, and amplitudes.

The color of noise refers to the power spectrum of a noise signal (a signal produced by a stochastic process). Different colors of noise have significantly different properties: for example, as audio signals they will sound different to human ears, and as images they will have a visibly different texture. This sense of 'color' for noise signals is similar to the concept of timbre in music (which is also called "tone color"); however the latter is almost always used for sound, and may consider very detailed features of the spectrum. The practice of naming kinds of noise after colors started with white noise, a signal whose spectrum has equal power within any equal interval of frequencies. Other noise colors include pink, red, and blue. Some of those names have standard definitions in certain disciplines. Many of these definitions assume a signal with components at all frequencies, with a power spectral density per unit of bandwidth proportional to 1/f β and hence they are examples of power-law noise. The Federal Standard 1037C Telecommunications Glossary defines white, pink, blue, and black noise. Even then, noise can have different patterns. Continuous noise is noise that is produced continuously without interruption. Intermittent noise is a noise level that increases and decreases rapidly. Impulsive noise is as sudden burst of noise.

In one or more embodiments, the methods and systems of the present invention provide for altering the frequency of a signal processed through a transducer. In one or more embodiments, the signal may include scanning a frequency within a predetermine frequency (Hertz or Hz) range to achieve a desired effect. In one or more embodiments, two or more transducers are used simultaneously. In one or more embodiments, the multiple transducers may comprise identical Hz ranges, a predetermined set of different Hz ranges, or a variable Hz ranges. In one or more embodiments, the multiple transducers allow a user to tune one frequency relative to another frequency and receives feedback from the output frequencies to analyze those frequencies and provide equalization, compression, and phase variation.

In another aspect, the present disclosure provides an apparatus for elastography that includes a vibratory member configured to be positioned adjacent to the surface of an imaging subject and configured to impart mechanical energy into tissue or materials of the subject. An acoustic energy source is also included and is externally coupled to the vibratory member, thereby causing the vibratory member to generate shear waves within the subject.

In one aspect, a High Definition ViscoElastography (HDVE) inertial driver apparatus includes two or more HDVE inertial driver devices. Each HDVE inertial driver device has: (i) a driver interface that enables receiving a driver signal from a controller; (ii) a resonating surface; and (iii) an inertial driver communicatively coupled to the driver interface and mechanically coupled to the resonating surface to independently generate a resonating displacement of the resonating surface. A support member of the HDVE inertial driver apparatus positions the two or more HDVE inertial driver devices into acoustic contact with a body to produce a shear wave field through a volume of tissue within a body or a volume of material within an object.

In an additional aspect, an imaging system of the present invention includes the HDVE inertial driver apparatus. A controller is communicatively coupled to the respective driver interfaces of the two or more HDVE inertial driver devices. The controller generates independent sequenced driver signals for each of the two or more driver interfaces to induce the shear wave field comprising a selected one of: (i) crawling waves; (ii) reverberant waves; and (iii) monodirectional waves in an acoustic frequency range of 20 Hz to 80 kHz with power sufficient to produce a displacement in a range of 0.5 to 50 μm. the imaging system includes an acoustic sensor positioned on the body and an acoustic frequency analyzer that is communicatively coupled to the acoustic sensor.

The controller generates multiple frequency waveform signals and amplifies them into driver signals to drive the HDVE inertial driver devices to produce a shear wave field for measuring tissue elasticity and viscoelasticity based on frequency response by the acoustic frequency analyzer.

In a further aspect, a method includes generating multiple frequency waveform signals and amplifying them to be used as drive signals. The method includes driving an inertial driver of respective HDVE inertial driver devices that produce resonating displacement of a resonating surface held against a body. The method includes receiving acoustic waves by an acoustic sensor held against the body. The method includes analyzing a frequency response for frequencies of the multiple frequency wave signal that passed through tissue of the body to measure tissue elasticity.

In one or more embodiments, the method includes generating driver signals coupled to each HDVE inertial driver device apparatus to produce a shear wave field through a volume of tissue within the body comprising a selected one of: (i) crawling waves; (ii) reverberant waves; and (iii) monodirectional waves in an acoustic frequency range of 20 Hz to 80 kHz with power sufficient to produce a displacement in a range of 0.1 to 50 μm. In one or more embodiments, the acoustic frequency range can be fewer than 20, 18, 16, 14, 12, 10 Hz, depending on the size of the object to be measured. In one or more embodiments, the method includes generating driver signals for a large body (e.g., elephant, building bearing, bridge bearing, etc.) wherein the frequency is 10 Hz or lower. In one or more embodiments, the method includes generating driver signals for seismic analysis, wherein the frequency is 0.1 Hz or lower. The method includes measuring elasticity and viscosity based on an analysis of the shear wave field.

In a further aspect, a system is provided comprising a multichannel tactile resonator having an array of transducers. In one or more embodiments, the system includes a flexible array of broadband (or full frequency range) inertial drivers placed around the exterior of the subject of interest in such a way as to produce a desired shear wave field throughout the interior region of interest of the subject. In one or more embodiments, the arrays have only one type of element optimized for lower frequency ranges. In one or more embodiments, the arrays have only one type of element optimized for higher frequency ranges. In one or more embodiments, the arrays have some elements for lower frequencies and some elements for higher frequencies. In one or more embodiments, the arrays are all flexible, by using springs and/or elastic supports and harnesses, so that they conform to the body's or object's exterior surface near the area of interest. In one or more embodiments, the array of inertial drivers are placed on the exterior of the subject and produce displacements of at least 0.5 micrometers in the interior region of interest. In one or more embodiments, the array comprises both low and high frequency elements. In one or more embodiments, the array produces a reverberant shear wave field inside the subject in a specified region of interest. In one or more embodiments, the array further comprises thermal protection for the drivers.

In one or more embodiments, the array comprises audio wave inertial drivers for imparting shear waves from a distance of the subject. For example, when used near an MRI, the inertial drivers cannot be near the machine so the array is placed at a distance and the shear waves imparted remotely In one or more embodiments, the array comprises audio wave inertial drivers for imparting shear waves from a distance of the subject using frequencies at least about 25 to about 35 KHz. In one or more embodiments, the array comprises audio wave inertial drivers for imparting shear waves from a distance of the subject using frequencies at least about 50 to about 60 KHz and used with an x-ray detector having a speed of at least about 90, 100, 120, 140, 160, 180K or more frames/second.

In one or more embodiments, the detectors are conventional or single energy CT (SECT) utilizing a single polychromatic X-ray beam (ranging from 70 to 140 kVp with a standard of 120 kVp) emitted from a single source and received by a single detector. In one or more embodiments, the detectors are dual energy CT (DECT), also known as "spectral imaging," wherein two energy levels (typically 80 and 140 kVp) are used to acquire images that can be processed to generate additional datasets.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Figure 1:
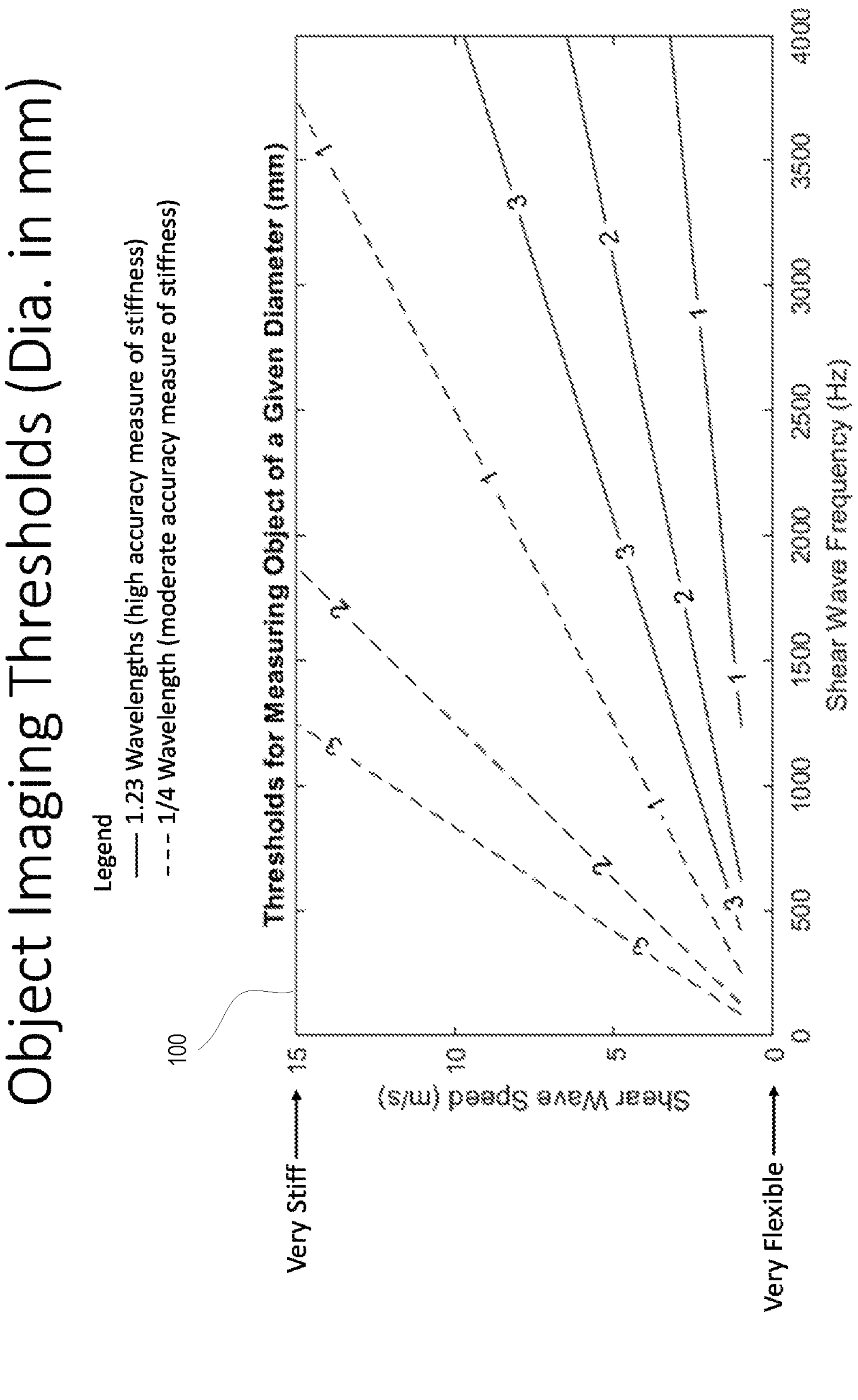
FIG. 1 is a graphical plot 100 approximate elastography image resolution in soft tissue as a function of shear wave frequency and lesion stiffness. Plot shows contours of approximate smallest diameter object detectable in soft tissue over a range of shear wave frequencies and object stiffnesses, for a desired level of measurement accuracy (moderate and high) of the object's stiffness (with stiffness represented as shear wave speed in meters per second)

According to aspects of the present disclosure, a device, system and method improve outcomes and reduce costs through objective imaging of the viscoelastic mechanical properties of tissue. Viscoelastic imaging provides key mechanical properties of tissue. Elastography imaging is an imaging modality that maps the elastic properties of tissue by inducing shear waves in the body, tracking the progression of the shear waves with an imaging modality, and calculating the elastic and/or viscous properties and displaying one or the other or a combination as a color map overlaid on the standard image produced by the imaging modality and system. A viscosity image maps the viscous properties of tissue, typically by obtaining simultaneous multi-frequency elastographies and then calculating dispersion (as that word is used in the field of Elastography) from the set of elastographies. Premise elasticity (often in the form of "stiffness", its inverse) and viscosity ("resistance to flow") differentiate healthy from unhealthy tissues. The present disclosure provides external high definition viscoelastography (HDVE) inertial drivers to induce shear waves throughout the tissue, including in the deepest parts of the tissue, and over a larger range of frequencies compared to typical viscoelastography imaging frequencies, including significantly higher frequencies, as a diagnostic imaging tool for disease states that alter viscoelastic mechanical properties.

Current ultrasound viscoelastography imaging has insufficient resolution and/or physical limitations that restrict its use, requiring more expensive, more invasive diagnostics. The current, most commonly used form of clinical ultrasound elastography (ARFI-based elastography) provides only shallow tissue imaging (up to 6 cm deep) to prevent overheating the tissue, and it is limited in resolution because the shear wave frequency components produced under safe conditions in tissue are mostly under 500 Hz and rapidly decrease to under 200 Hz after propagating only a few millimeters from the ARFI focus point. Magnetic resonance imaging (MRI) elastography provides only poor spatial resolution too, because shear wave induction motors must be operated at a safe distance from the MRI magnets, which generally limits shear wave frequencies to under 120 Hz at the patient. Generally-known approaches create echoic reverberations that cause degraded images near tissue boundaries. Generally known ultrasound and MRI elastography uses a narrow range of frequency measurements which provides unreliable viscosity measurements. In particular, generally-known approaches are used clinically with shear wave frequencies ranging from 30-120 Hz, which can achieve only about 1.5 cm resolution for elasticity and only poor measurements of viscosity. It is believed that some successful attempts have been made up to 180-200 Hz, which should improve the resolution by only about 30%. Conventionally it is believed that nothing diagnostically useful was to be gained by operating with shear wave frequencies over approximately 180 Hz.

The present disclosure provides external HDVE inertial drivers to generate higher vibration frequencies for significantly better spatial resolution and more reliable viscosity estimates. The external HDVE inertial drivers induce shear waves in the tissue with broad range of frequencies for reliable viscosity measurements and for improved resolution. Thus, the present disclosure provides: (i) ability to image tissues to the full scan depth of ultrasound; (ii) deep tissue resolution (e.g., in liver) over four to ten times better than traditional elastography; (iii) near field surface tissue resolution (e.g., in breast) over ten times better than traditional elastography (i.e., 1-3 mm resolution); (iv) ability to image echoic tissues (e.g. kidney capsule); and (v) more reliable measures of viscosity and viscosity (dispersion) maps. In one or more exemplary implementations, the HDVE inertial drivers induce shear waves ranging from below 0.1 Hz up to above 80,000 Hz, so that when using current common clinical ultrasound probes, for breast ultrasound viscoelastography, ranges from 40-5,000 Hz can be induced and measured, and in liver ultrasound viscoelastography, ranges from 40-3,000 Hz can be measured. These frequencies contemplate that the acoustic (ultrasound) waves have to travel 5 cm into the body (to image the full breast tissue) then 5 cm back to the acoustic sensor, and have to travel 14 cm into the body (to image the full liver) then 14 cm back to the acoustic sensor.

As compared to convention 40 Hz that results in low resolution, the present innovation supports an informative 1-3 mm resolution, with the resulting amount of resolution affected by the stiffness of the objects imaged within the tissue (and by tissue, unless stated otherwise, we mean soft tissue). The above provided vibration frequencies for breast and liver support this range of resolution.

Thereby, the present innovation improves upon existing imaging application and anticipates potential opportunities for new imaging applications such as:

(i) deep liver viscoelastography that can identify all stages of non-alcoholic steatohepatitis (NASH);

(ii) The 1-3 mm resolution enables ultrasound viscoelastography to be a potential alternative to breast mammography with no ionizing X-rays and no discomfort, potentially replacing the need for biopsy;

(iii) if utilized with reverberant shear wave viscoelastography, echoic tissues like kidney can be imaged, wherein changes in renal microcellular viscosity is an important indicator in certain kidney cancers;

(iv) ultrasound viscoelastography is a generalized radiology tool with many other applications such as prostate cancer detection, thyroid, spleen, cornea, testicle, muscle, ligament, tendon, guided biopsy, therapy monitoring, etc.;

(v) specialized versions can be used for applications such as (a) cardiac wall stiffness imaging to map damaged heart tissue and (b) vascular wall stiffness imaging; and (vi) non-medical applications such as non-destructive testing of bridge and building bearings, and subterranean imaging.

In one or more embodiments, the imaging application can preferably make adjustments according to a desired effect. Exemplary adjustments include adjusting tonal frequencies, adjusting modulation of frequencies between tactile points, storing tonal presets, and returning sonic, tonal or visual stimuli based on the feedback information. In one or more embodiments, the device application is capable of enhancing frequencies and shifting media pitch to accommodate a user's frequency preferences. In various alternative embodiments, the apparatus may include an adjustable EQ filter sending prescribed frequencies to tactile output. In some applications, this system has a matrix control which will switch the left/right orientation in different ways.

Shear Waves have the following aspects: (i) the higher the frequency the smaller the wavelength; (ii) the smaller the wavelength the better the resolution; (iii) generally it is thought that ¼ wavelength needs to fit inside an object for moderate accuracy stiffness measurement; and (iv) approximately 1.24 wavelengths need to fit inside the object for high accuracy stiffness measurement.

Comparison of Shear Waves generated by HDVE inertial drivers vs. shear waves generated by acoustic radiation force impulse (ARFI) is as follows. ARFI provides: (i) 95% of shear wave power spectrum <500 Hz and decreases rapidly with distance & depth which limits resolution; (ii) conventionally 6 cm depth with newer approaches going somewhat deeper but with less resolution; and (iii) small field of view. By contrast, HDVE inertial drivers have the following attributes: (i) 0.1 to 80,000 Hz with full power spectrum enabling 1-3 mm resolution of stiff objects within soft tissues and with reliable viscosity measurements; (ii) full depth penetration; and (iii) full field of view. Experimental use has demonstrated that: (i) software and hardware solutions are robust and reliable; (ii) have achieved deep tissue multifrequency reconstructions such as in human liver, kidney, thyroid, breast and tendon; (iii) demonstrated higher frequency shear waves than other methods, which translates to dramatically better resolution & improved viscosity estimates.

According to aspects of the present innovation, method and apparatuses are provided for inducing shear waves with frequency-specific sine, square and triangle waveforms, and with complex waveforms (including noise) into human tissue, and are embodied in flexible or elastic, bed, vest, body harness or handheld application system, consisting of one or more materials such as rubber and plastic, for the purpose of exciting various regions and structures within the target tissue or material, for use in elastography and viscoelastography imaging using ultrasound and other elastography- and viscoelastography-applicable imaging modalities including but not limited to optical coherence tomography (OCT), computed tomography (CT), X-ray, and magnetic resonance imaging (MRI) systems when coupled with appropriate adapters and extensions. A clamp with one or more HDVE inertial drivers, power amplifiers and digital signal processing, conforming to and in contact with the body or object, inducing a non-invasive shear wave field including but not limited to Reverberant Shear Wave Fields, Crawling Wave Fields, and other elastography- and viscoelastography-applicable shear wave fields, within the body or objects, which is then scanned by ultrasound or other imaging modality as applicable. Distinctions in elastic and viscous properties of various structures, nodes, lumps and abnormalities become visible within a region(s) of interest. The system can also induce frequency-specific, non-frequency-specific (noise), and complex longitudinal and shear waves, following typical wave paths of compression and rarefaction. Frequency of waveforms is specific to each type and density of tissue and flexible or elastic material.

Multiple frequency signals produced by HDVE inertial drivers may include single frequency waveforms or complex (or arbitrary) waveforms. Complex waveforms are comprised of more than one frequency such as a natural overtone series, a major chord, a minor chord, and other series, and are essential to measuring viscosity. Multiple sources are essential for creating a variety of shear wave fields such as reverberant shear waves, crawling waves, and many other shear wave fields.

Sound is a vibration that propagates as an audible or tactile wave of pressure, through a transmission medium such as a gas, liquid or solid. Each pressure wave causes increased and decreased pressure called compression and rarefaction. Without a transmission medium, sound does not exist. Sound is defined as an oscillation in pressure, stress, particle displacement, particle velocity, etc., propagated in a medium with internal forces (e.g., elastic or viscous), or the superposition of such propagated oscillation. (Sound traveling through a non-elastic media is simply transferred through the media, often with minimal attenuation.)

Sound can propagate through a medium such as air, water and solids as longitudinal waves and also as a transverse (shear) wave in solids. The sound waves are generated by a sound source, such as the vibrating diaphragm of a loudspeaker or a tactile shaker. The sound source creates vibrations in the surrounding medium. As the source continues to vibrate the medium, the vibrations propagate away from the source at the speed of sound, thus forming the sound wave. At a fixed distance from the source, the pressure, velocity, and displacement of the medium vary in time. At an instant in time, the pressure, velocity, and displacement vary in space. Note that the particles of the medium do not travel with the sound wave. This is intuitively obvious for a solid, and the same is true for liquids and gases (that is, the vibrations of particles in the gas or liquid transport the vibrations, while the average position of the particles over time does not change). During propagation, waves can be reflected, refracted, or attenuated by the medium.

The behavior of sound propagation is generally affected by three things: (i) a complex relationship between the density and pressure of the medium, which is affected by temperature, determines the speed of sound within the medium; and (ii) motion of the medium itself. If the medium is moving, this movement may increase or decrease the absolute speed of the sound wave depending on the direction of the movement. For example, sound moving through wind will have its speed of propagation increased by the speed of the wind if the sound and wind are moving in the same direction. If the sound and wind are moving in opposite directions, the speed of the sound wave will be decreased by the speed of the wind, referred to as the "Doppler effect"; and (iii) the viscosity of the medium. Medium viscosity determines the rate at which sound is attenuated. For many media, such as air or water, attenuation due to viscosity is negligible. Sound, on the other hand, does not travel well through a lump of soft clay.

When sound is moving through a medium that does not have constant physical properties, it may be refracted (either dispersed or focused) or attenuated at varying rates. Sound is transmitted through gases, plasma, liquids and solids primarily as longitudinal waves, also called compression waves. It requires a medium to propagate. Longitudinal sound waves are waves of alternating pressure deviations from the equilibrium pressure, causing local regions of compression and rarefaction, while transverse waves (in solids) are waves of alternating shear stress at right angle to the direction of propagation. In all mediums, depending on the density of the material, transverse waves (also known as sheer waves) are produced and travel at a much slower rate than longitudinal.

The energy carried by an oscillating sound wave converts back and forth between the potential energy of the extra compression (in case of longitudinal waves) or lateral displacement strain (in case of transverse waves) of the matter, and the kinetic energy of the displacement velocity of particles of the medium.

Sound waves are often simplified to a description in terms of sinusoidal plane waves, which are characterized by these generic properties: (i) Frequency, or its inverse, wavelength; (ii) Amplitude: sound pressure or intensity in the medium; (iii) Speed of sound; and (iv) Direction.

The speed of sound is affected by the transmission medium and is a fundamental property of the material. Those physical properties and the speed of sound change with ambient conditions. At 68° F., sound travels on average at 1,127 fps through air, 4,805 fps through water and 16, 850 fps through steel. Human tissue would fall somewhere in the range of water, depending on the structure of the tissue, with a range between soft tissue to bone or calcified mass. The speed of sound is also slightly sensitive, being subject to a second-order enharmonic effect, to the sound amplitude, which means there are non-linear propagation effects, such as the production of harmonics and mixed tones not present in the original sound.

Sound is made up of a single or combination of frequencies, which are determined by the speed of the wave. A continuous 1 Hz sine wave vibrates in its medium for one second per wave. A 500 Hz wave vibrates 500 times per second. Each frequency provides a "pitch". Audible pitches for humans are perceived, on average, between 20 and 20,000 Hz. A single waveform may also contain many frequencies of varying amplitudes and phase.

Multiple frequencies coming from two or more sources affect each other in the medium. A piano tuner, for example, tunes the individual strings of one single note, not only by comparing the string to a reference pitch (such as A above middle C as 440 Hz) but he listens for the effect of "beating" as the strings are brought into tune with each other. Two strings that are slightly out of tune with each other will produce an acoustic beating. When the strings are brought into tune, the beating stops.

In acoustics, a beat is an interference pattern between two sounds of slightly different frequencies, produced as a periodic variation in volume whose rate is the difference of the two frequencies. Tuning two tones to a unison will present a peculiar effect: when the two tones are close in pitch but not identical, the difference in frequency generates the beating. The amplitude varies like in a tremolo as the sounds alternately interfere constructively and destructively. As the two tones gradually approach unison, the beating slows down. As the two tones get further apart, their beat frequency increases until the interference stops This phenomenon is best known in acoustics or music, though it can be found in any linear system: "According to the law of superposition, two tones sounding simultaneously are superimposed in a very simple way: one adds their amplitudes". When the two waves are nearly 180 degrees out of phase the maxima of one wave cancel the minima of the other, whereas when they are nearly in phase their maxima sum up, raising the amplitude.

If the two original frequencies are quite close (for example, a difference of approximately twelve hertz), the frequency of the cosine of the right side of the expression above, that is $f1-f2/2$, is often too low to be perceived as an audible tone or pitch. Instead, it is perceived as a periodic variation in the amplitude of the first term in the expression above. It can be said that the lower frequency cosine term is an envelope for the higher frequency one, i.e. that its amplitude is modulated. The frequency of the modulation is $f1+f2/2$, that is, the average of the two frequencies. It can be noted that every second burst in the modulation pattern is inverted. Each peak is replaced by a trough and vice versa.

Beating can also be heard between notes that are near to, but not exactly, a harmonic interval, due to some harmonic of the first note beating with a harmonic of the second note. For example, in the case of perfect fifth, the third harmonic (i.e. second overtone) of the bass note beats with the second harmonic (first overtone) of the other note. As well as with out of tune notes, this can also happen with some correctly tuned equal temperament intervals, because of the differences between them and the corresponding just intonation intervals.

Crawling Wave ultrasound elastography imaging is based on the use of two or more shear wave frequencies which produce a "beating" effect in tissue. Two shear waves, for example, may produce waveforms slightly apart (in music, this would be called "out-of-tune"), at, for example 200 Hz and 199.5 Hz, which produces a beating pattern in tissue, which effects the corresponding relationship between longitudinal and transverse (shear) waves, causing the image to "crawl" or move across the ultrasound screen. With reverberant viscoelastography, these properties become more complex and novel.

Multiple HDVE inertial drivers are used to produce an infinite number of complex interference and phasing waveform patterns within human tissue, at depths and strengths new to the art. This enables the crawling wave, reverberant and other imaging methods to take advantage of an infinite variety of combinations and effects, as each combination of waveforms will affect tissue differently, depending the elasticity and viscosity of the tissue. When two or more HDVE inertial drivers are 180° out-of-phase with each other, there is a mechanical movement that occurs, or a "rocking" back and force due to the mechanical opposing pressure of each waveform. This effect, and any number of combinations of phasing, is also useful for crawling wave, reverberant and other imaging methods. HDVE inertial driver systems also have directionality characteristics and depending on frequency, can be useful with targeting (beam steering) the waveform into specific areas of the body.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to devices for ultrasound elastography and viscoelastography, with extension to other compatible imaging modalities such as optical coherence tomography (OCT) imaging and magnetic resonance imaging (MRI).

In one or more embodiments, the illustrated embodiments are directed to external vibratory devices for use with a medical image diagnostic apparatus, which is any one of an ultrasound diagnostic apparatus, an x-ray diagnostic apparatus, an x-ray computed tomography (CT) apparatus, a magnetic resonance imaging (MRI) apparatus, a single photon emission computed tomography (SPECT) apparatus, a positron emission computed tomography (PET) apparatus, a SPECT-CT apparatus that is a combination of the SPECT apparatus and the x-ray CT apparatus, a PET-CT apparatus that is a combination of the PET apparatus and the x-ray CT apparatus, and a subject testing apparatus.

The ultrasonic probe is a portion that contacts a surface of a target object or is inserted into the body of the target object, and may transmit and receive ultrasonic waves. Specifically, the ultrasonic probe may transmit an ultrasonic wave to the inside of the target object according to a transmission signal provided from the main body, receive an echo ultrasonic wave reflected from a specific portion in the target object, and transmit the echo ultrasonic wave to the main body.

The ultrasonic probe may be connected through a cable to receive various signals required for controlling the ultrasonic probe or to transmit an analog signal or a digital signal corresponding to the ultrasonic echo signal received by the ultrasonic probe to the main body. However, the embodiment of the ultrasonic probe is not limited thereto, and the ultrasonic probe may be wirelessly connected to the main body. In this case, the ultrasonic probe may be implemented as a wireless probe. In addition, a plurality of the ultrasonic probes may be connected to the one main body.

The device may be configured to receive the user's input, and the user may input commands for starting diagnosis, selecting a diagnosis region, selecting a diagnosis type, and selecting a mode for an ultrasound image. Examples of modes for the ultrasound image include an A-mode (Amplitude mode), a B-mode (Brightness mode), a D-mode (Doppler mode), an E-mode (Elastography mode), and an M-mode (Motion mode). A display may be implemented using at least one of various display panels such as a liquid crystal display (LCD) panel, a light emitting diode (LED) panel, or an organic light emitting diode (OLED). It is also possible that the display is composed of two or more displays so that the respective displays may simultaneously display different images. For example, one display may display a 2D ultrasound image and the other display may display a 3D ultrasound image. Alternatively, one display may display a B-mode image and the other display may display a contrast agent image.

A user such as a doctor may perform diagnosis of a specific disease using the ultrasound image displayed on the display and the region for acquiring the ultrasound image may vary depending on the disease to be diagnosed. For example, an abdominal ultrasound image may be used to diagnose a fatty liver.

It is known that a fatty liver, which is a disease caused by fatty deposits in the liver, may develop into end stage liver disease such as hepatic cirrhosis or hepatocellular carcinoma as well as progress to steatohepatitis and hepatic fibrosis. In addition, since high prevalence rates of a fatty liver have been reported worldwide and in particular, a non-alcoholic fatty liver disease (NAFLD) is closely related to obesity and metabolic syndrome, the discovery of a fatty liver is a very important region in diagnosis using ultrasound images. The fatty liver may be found by measuring the viscoelasticity of liver tissue. Viscoelasticity is a property of coexistence of viscosity and elasticity, which means a property accompanied by elastic deformation and viscous flow. The viscoelastic property of the tissues in a living body, including the liver, may be measured by using an ultrasonic wave, specifically may be measured by detecting a shear wave.

When ultrasonic signals are strongly irradiated into a target object, the tissue may actually move finely, and shear waves are generated in the tissue due to the movement of the tissue. The shear waves generated by strong ultrasonic waves in the target object progress from a focus region to the periphery, where the progressing direction of the waves is lateral and the direction of vibration of the tissue particles is vertical. The velocity of the progressing shear waves changes according to the vibrational characteristics of a medium. Accordingly, the velocity of the shear waves is a main variable for measuring the elastic properties of the medium, that is, the elastic modulus.

Therefore, the velocity of the shear waves may be measured by continuously tracking the motion of the shear waves generated in the tissue, and the elastic modulus of the tissue may be estimated from the velocity of the shear waves. On the other hand, there may be a case where the tissue does not have pure elasticity but viscoelasticity having both elasticity and viscosity. For example, in the case of a fatty liver in which fat is accumulated in the liver, the liver has viscoelasticity having viscosity and elasticity rather than pure elasticity. In a case where the tissue has viscoelasticity, the attenuation of a shear wave amplitude may be additionally observed, as well as a dispersion phenomenon in which the speed of the shear wave varies depending on its frequency.

In this case, an attenuation phenomenon occurs in which the wave energy decreases as a wave progresses in the progressing shear wave. In general, as a wave progresses, it spreads spatially, widening the wave front, and reducing the energy of the wave. In addition, the energy of the waves is reduced because a physical phenomenon occurs in which the energy of the waves is absorbed into the medium while passing through the medium. The former is attenuation by geometric spreading, and the latter is attenuation by absorption into the medium. The critical attenuation in viscoelasticity is attenuation due to absorption into the medium. To compute this, it is necessary to compensate for the component due to a geometric spreading phenomenon in the observed attenuation.

The velocity of a shear wave is not constant for each frequency component, and a speed dispersion phenomenon that varies depending on the frequency occurs. The attenuation coefficient also shows a dispersion phenomenon (attenuation dispersion). Therefore, a system for measuring and displaying the viscoelastic property of a target object may include at least one parameter of a shear wave speed, a shear wave attenuation coefficient, a shear wave speed dispersion, a shear wave attenuation dispersion, a viscosity, and a shear modulus.

In one or more embodiments, the ultrasound imaging apparatus includes a transducer module for converting an electric signal into an ultrasonic signal or an ultrasonic signal into an electric signal, a beam former for generating a transmission beam and a reception beam, an image processor for generating an ultrasound image using an echo signal output from the beam former, a controller for controlling the operation of internal components of the ultrasound imaging apparatus, and one or more displays. The transducer module may convert an electric signal into an ultrasonic signal or an ultrasonic signal into an electric signal. To this end, the transducer module may comprise an ultrasonic transducer of various elements, and the ultrasonic transducer may be implemented as any one of a piezoelectric ultrasonic transducer using a piezoelectric effect of a piezoelectric material, a magnetostrictive ultrasonic transducer using a magnetostrictive effect of a magnetic material, a capacitive micromachined ultrasonic transducer (cMUT) that transmits and receives ultrasonic waves by using vibrations of several hundreds or thousands of micromachined thin films, and the like. In addition, other types of transducers capable of generating ultrasonic waves in accordance with electrical signals or generating electrical signals in accordance with ultrasonic waves may also be examples of ultrasonic transducers. Further, the transducer module may further include a switch such as a multiplexer (MUX) for selecting a transducer element to be used for transmitting and receiving ultrasonic signals. The transducer module 110 may be provided inside the ultrasonic probe.

As used herein, the term "acoustic" refers to infrasonic, sonic and ultrasonic vibrations and/or waves. Vibrations may comprise, but are not limited to, oscillatory mechanical motion of a rigid material, mechanical vibrations and/or waves propagating in an elastic or viscoelastic material, and pressure waves propagating within a hydraulic or pneumatic fluid.

As used herein, the term "acoustic energy" refers to energy stored in the form of acoustic vibrations or waves. The vibrations or waves may be transmitted through an elastic solid or a liquid or gas, with frequencies typically in the approximate range of 0.01 to 80,000 hertz and are capable of being detected.

As used herein, the term "acoustic energy source" refers to an actuator, driver, transducer or other device capable of generating acoustic vibrations and/or waves. Exemplary acoustic energy sources include, but are not limited to, electro-acoustic devices such as audio speakers, devices adapted to produce oscillatory linear motion such as linear motors, tactile transducers, piezoelectric transducers, ultrasonic transducers, magneto-acoustic transducers, pneumatic devices adapted to couple acoustic vibrations into a pneumatic fluid, surface acoustic wave transducers, micro-electro-mechanical systems and electromagnetic acoustic transducers.

As used herein, the terms "transducer", "audio transducer", "tactile audio transducers", "electro-mechanical vibration drivers", and "High Definition ViscoElastography (HDVE) inertial driver" refer to a vibration inducing apparatus for introducing frequency specific vibrations into a body or object. In one or more embodiments, the frequency specific vibrations induce deeper and faster shear waves than provided by known systems.

FIG. 1 is a graphical plot 100 of approximate elastography image resolution in soft tissue as a function of shear wave frequency and lesion stiffness. Plot shows contours of approximate smallest diameter object detectable in soft tissue over a range of shear wave frequencies and object stiffnesses, for a desired level of measurement accuracy (moderate and high) of the object's stiffness (with stiffness represented as shear wave speed in meters per second). Tissue has three mechanical properties: (i) density, which is generally unchanging in soft tissue and can be measured by X-ray imaging; (ii) stiffness (the inverse of Young's Modulus) like a spring, can often be used to distinguish between healthy tissue and scarring and other diseased or damaged tissues; and (iii) viscosity (resistance to flow), often modeled as a dash pot, likely provides useful diagnostic information. The present disclosure provides a non-invasive approach to determining stiffness and viscosity.

Figure 2A:
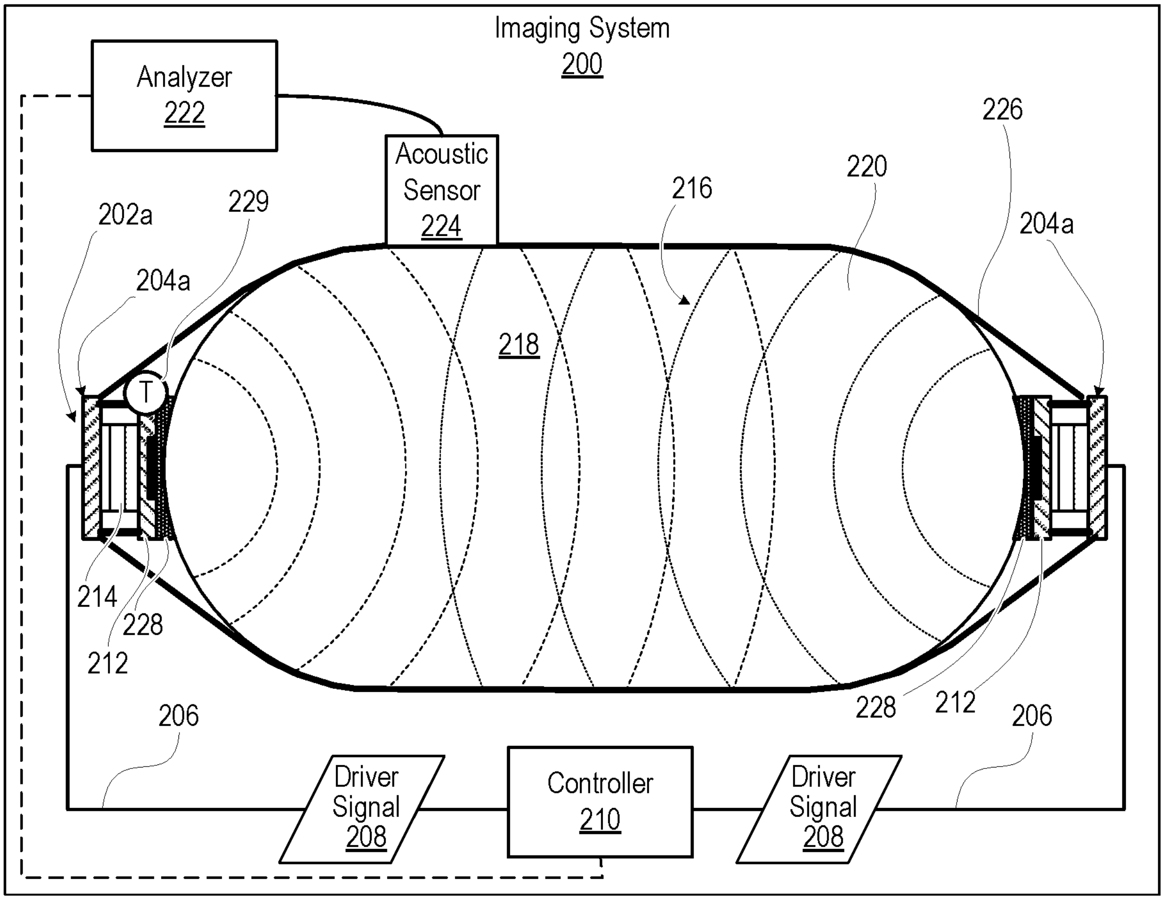
FIG. 2A is a block diagram of an imaging system having a High Definition ViscoElastography (HDVE) inertial driver apparatus including a harness as support member, according to one or more embodiments.

FIG. 2A is a block diagram of an imaging system 200*a* having a High Definition ViscoElastography (HDVE) inertial driver apparatus 202*a* that includes two or more HDVE inertial driver devices 204. Each HDVE inertial driver device 202 includes a driver interface 206 that enables receiving a driver signal 208 from a controller 210. Each HDVE inertial driver device 204 includes a respective resonating surface 212. Each HDVE inertial driver device 204 includes an inertial driver 214 that is communicatively coupled to the driver interface 206 and mechanically coupled to the resonating surface 212 to independently generate a resonating displacement of the resonating surface 212.

The controller 210 is communicatively coupled to the respective driver interfaces 206 of the two or more HDVE inertial driver devices 204. The controller 210 generates he independent sequenced driver signals 208 that induce a shear wave field 216 within tissue 218 of a body 220. the shear wave field 216 is a selected one of: (i) crawling waves; (ii) reverberant waves; and (iii) monodirectional waves. The shear wave field 216 is in an acoustic frequency range of 20 Hz to 80 kHz with power sufficient to produce a displacement in a range of 0.1 to 50 μmm.

An acoustic frequency analyzer 222 is communicatively coupled to an acoustic sensor 224. The controller 210 generates multiple frequency waveform signals for the acoustic frequency analyzer 222 to measure tissue elasticity based on frequency response. The controller 210 generates the driver signals that produce the shear wave field 216 for measuring viscosity by the acoustic frequency analyzer 222.

A support member adjustably positions the two or more HDVE inertial driver devices 204 into acoustic contact with the body 220. In one or more embodiments, the support member is a harness 226 that holds the HDVE inertial driver device 204 against the body 220 by encircling the body 220. The harness 226 can include adjustment and engagement features to fit on different sizes of bodies 220. In one or more embodiments, at least one resonating surface 212 includes a resilient surface 228 that conforms to the body 220 and that is acoustically transmissive.

In one or more embodiments, a temperature sensor 229 is coupled to one of the two or more HDVE inertial driver devices 204*a*. The controller 236 is communicatively coupled to the temperature sensor 242 to respond to a temperature measurement by the temperature sensor 242. The controller 236 reduces an amount of power of a selected independent driver signal 206 to mitigate control temperature of the corresponding resonating surface 210*a*-210*d*.

Figure 2B:
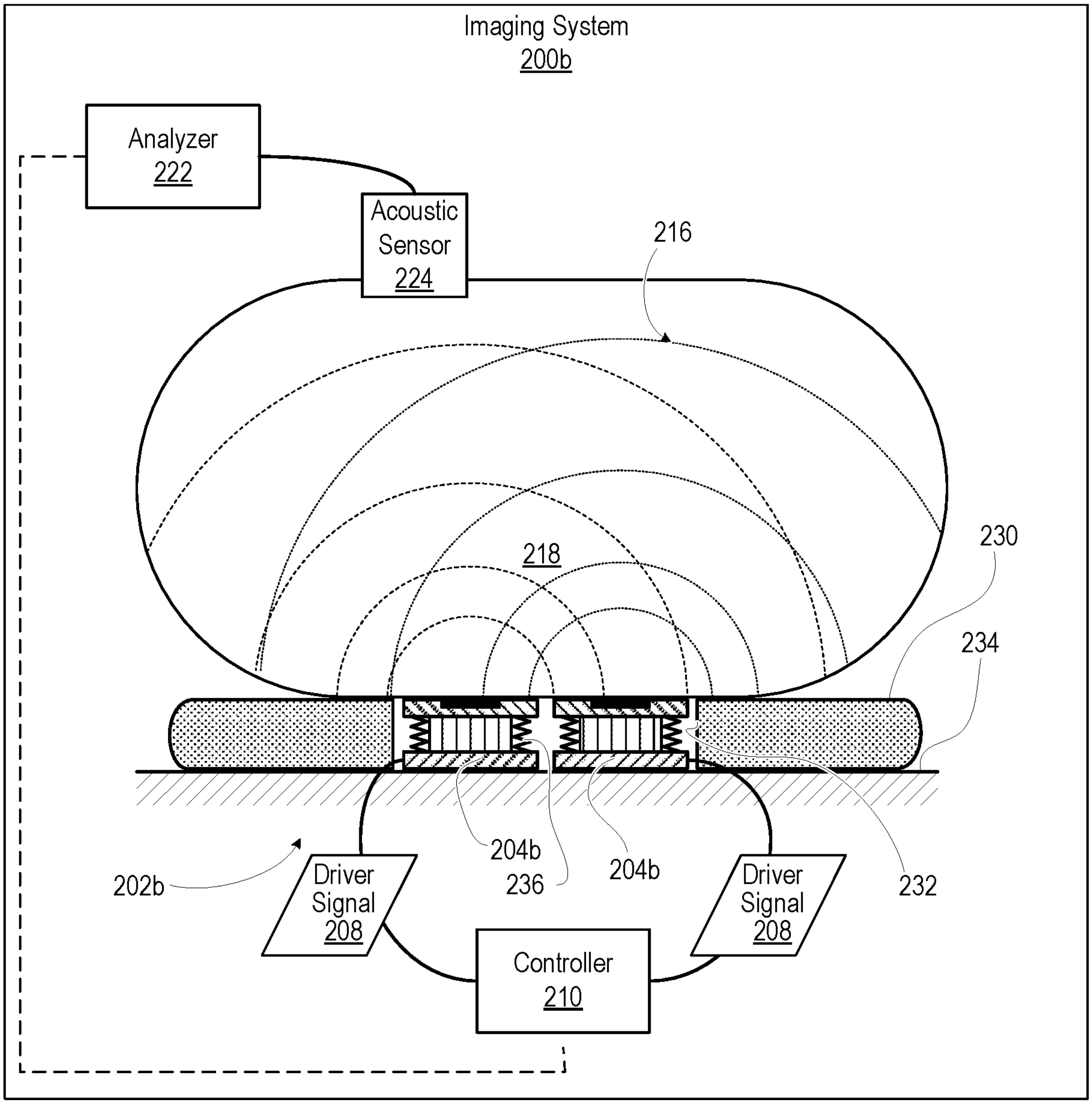
FIG. 2B is a block diagram of an imaging system having HDVE inertial driver apparatus including a flexible substrate as support member, according to one or more embodiments.

In one or more embodiments, FIG. 2B illustrates an imaging system 200*b* having an HDVE inertial driver apparatus 202*b* that includes controller 210, analyzer 222, and acoustic sensor 224. The body 220 is supported by a flexible substrate such as a resilient mat 230 having an aperture 232 through which HDVE inertial driver devices 202*b* contact the body 220. The resilient mat 230 and HDVE inertial driver devices 202*b* in turn rest upon a support surface 234, such as a table or floor. In one or more embodiments, the support member of each HDVE inertial driver device 202*b* is a compression member 236, such as a plurality of springs of a HDVE inertial driver device 202*b*, that enables the resonating surface 212 to conform to the body 220 that rests upon the HDVE inertial driver devices 202*b*.

Figure 2C:
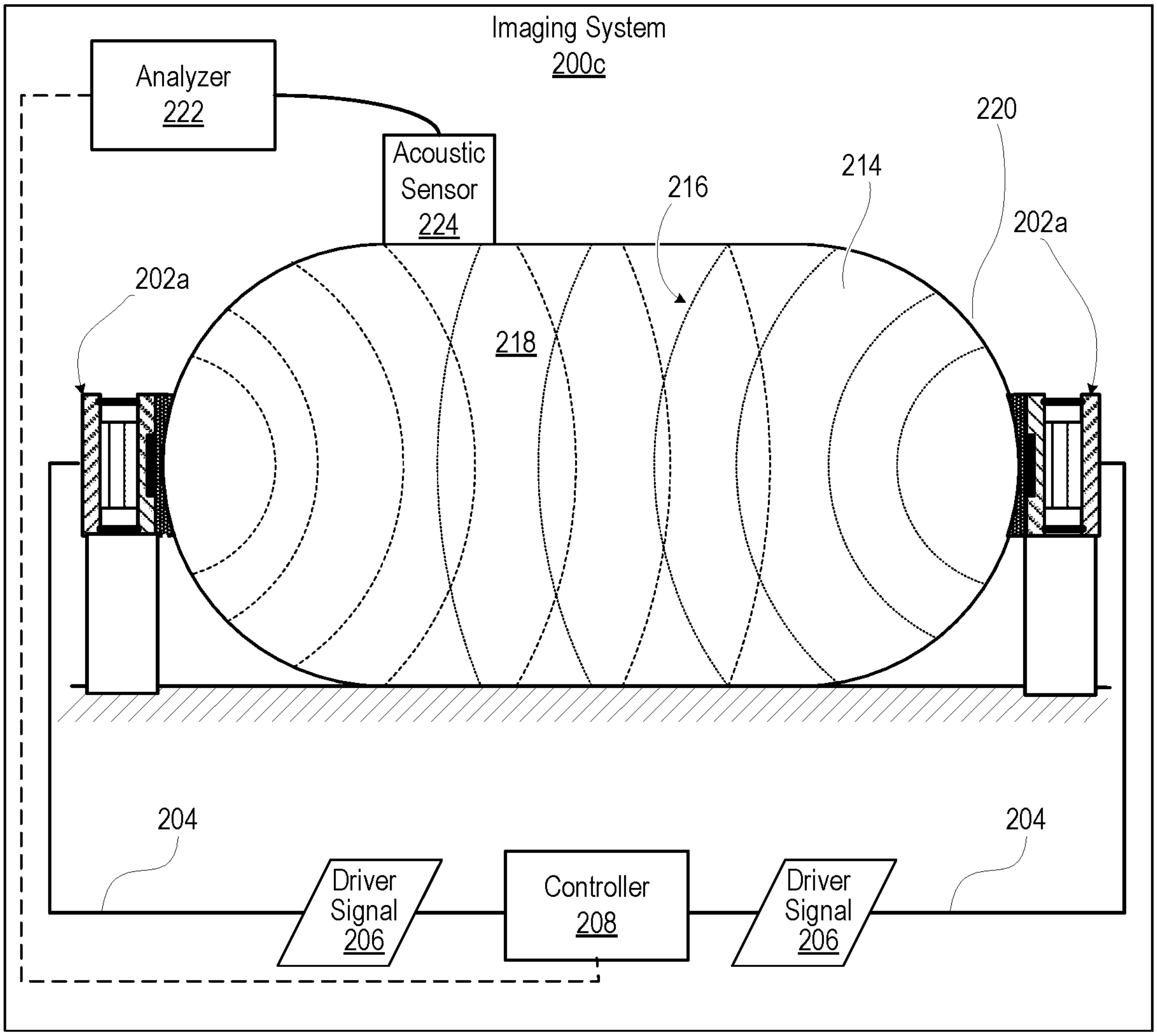
FIG. 2C is a block diagram of an imaging system having HDVE inertial driver apparatus including a pair of clamps as a support member, according to one or more embodiments.

In one or more embodiments, FIG. 2C illustrates an imaging system 200*c* having an HDVE inertial driver apparatus 202*c* that includes controller 210, analyzer 222, and acoustic sensor 224. The body 220 is supported the support surface 234, such as a table. In one or more embodiments, the support member of each HDVE inertial driver device 204*c* is a corresponding pair of clamps 240 attached to the support surface 234. At least one end of the pair of clamps 240 is adjustable to provide acoustic contact to the body 220. In one or more embodiments, the pair of clamps 240 provide a heat sink path to draw heat away from the body 220. In one or more embodiments, in addition to an adjustment mechanism 236, the clamps 240 can be springy, allowing for slight changes in the spacing across the body 220.

Figure 2D:
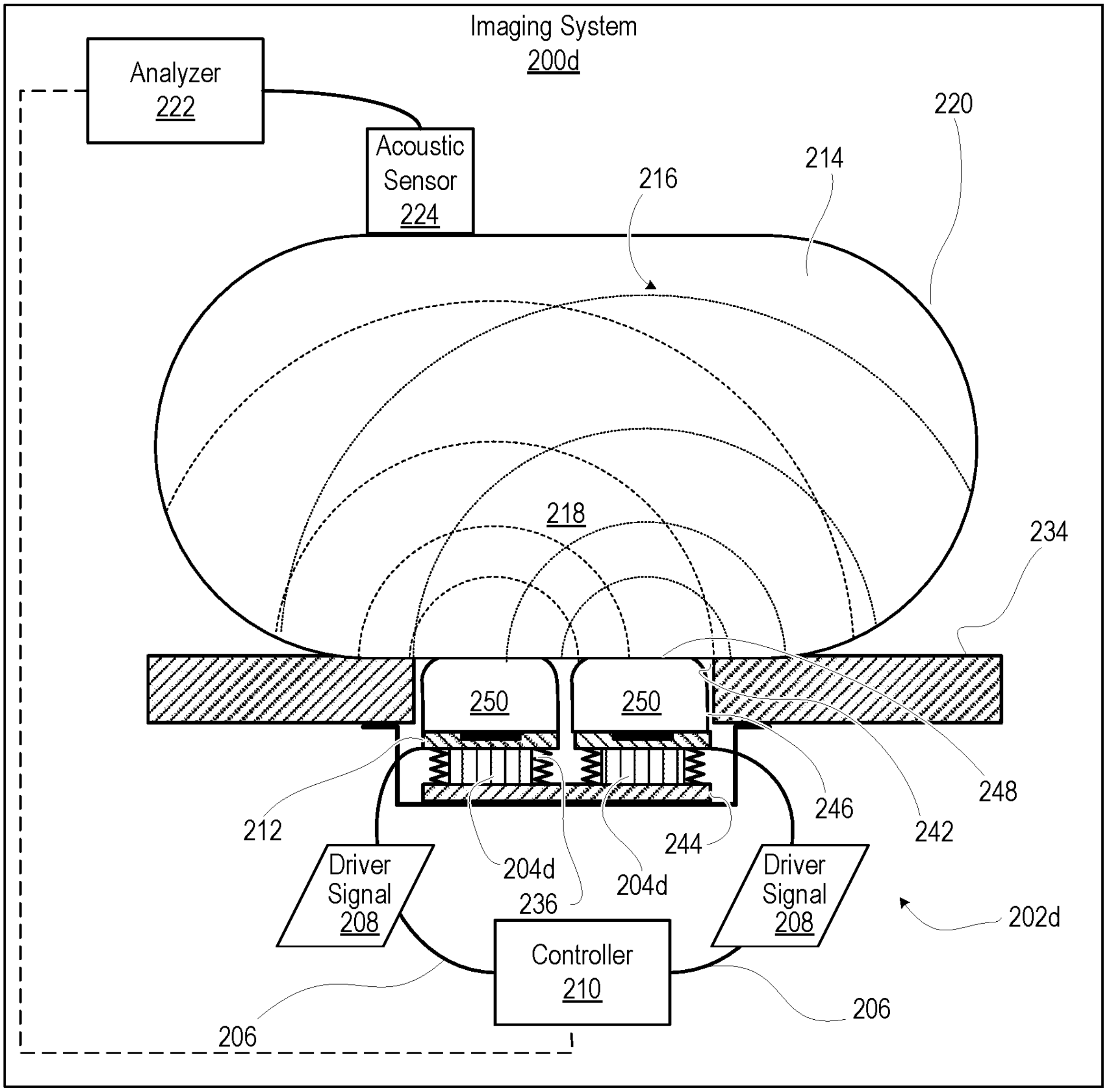
FIG. 2D is a block diagram of an imaging system having HDVE inertial driver apparatus including table mounted HDVE inertial driver devices, according to one or more embodiments.

In one or more embodiments, FIG. 2D illustrates an imaging system 200*d* having an HDVE inertial driver apparatus 202*d* that includes controller 210, analyzer 222, and acoustic sensor 224. The body 220 is supported the support surface 234, such as a table, having an aperture 242. Two or more HDVE inertial driver devices 204*d* are positioned within the aperture 242 and having a unitary base 244 attached to the support surface 234. In one or more embodiments, at least one resonating surface 212 is encompassed by a housing 246 having a contact surface 248 that contacts the body 220. The housing 246 contains a sealed air column 250 separating the resonating surface 212 from the contact surface 248 and minimizing the separation to under 1 cm, preferably under 0.5 cm, and most preferably under 0.25 cm.

Figure 2E:
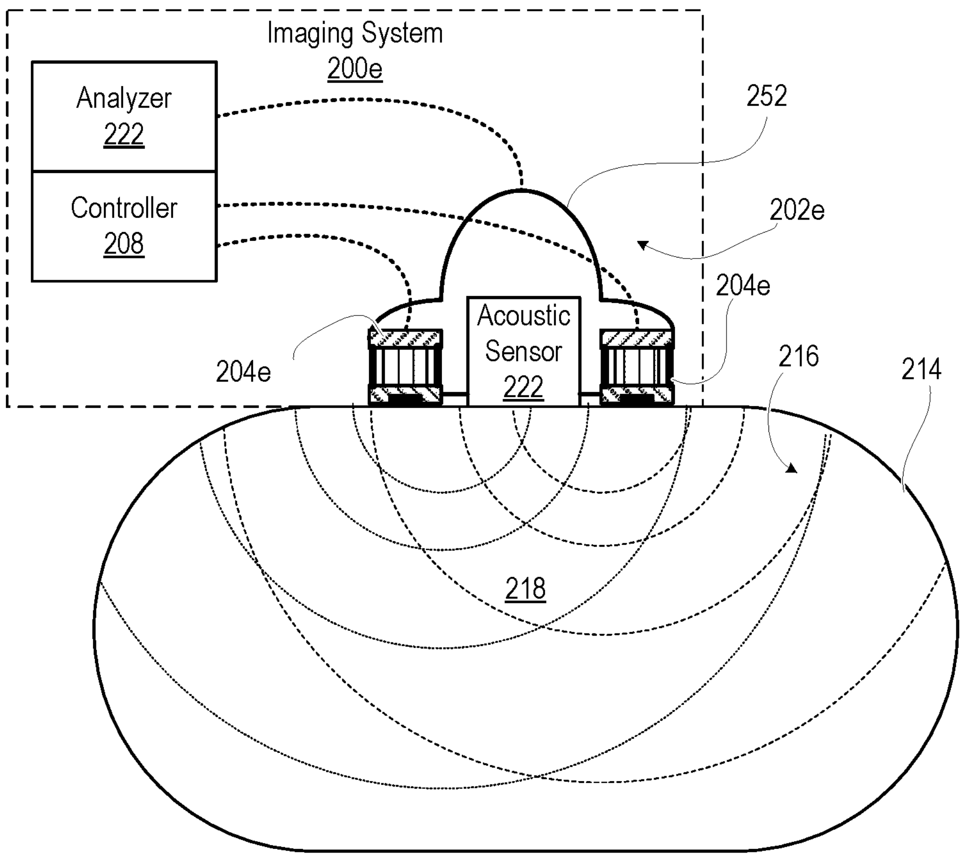
FIG. 2E is a block diagram of an imaging system having HDVE inertial driver apparatus and acoustic sensor mounted in a probe housing, according to one or more embodiments.

In one or more embodiments, FIG. 2E illustrates an imaging system 200*e* having an HDVE inertial driver apparatus 202*e* installed within a probe housing 252 that also positions the acoustic sensor 224 between two HDVE inertial driver devices 204*e*. The controller 210 and analyzer 222 are communicatively coupled through the probe housing 252 respectively to the two HDVE inertial driver devices 204*e* and the acoustic sensor 224.

Figure 3:
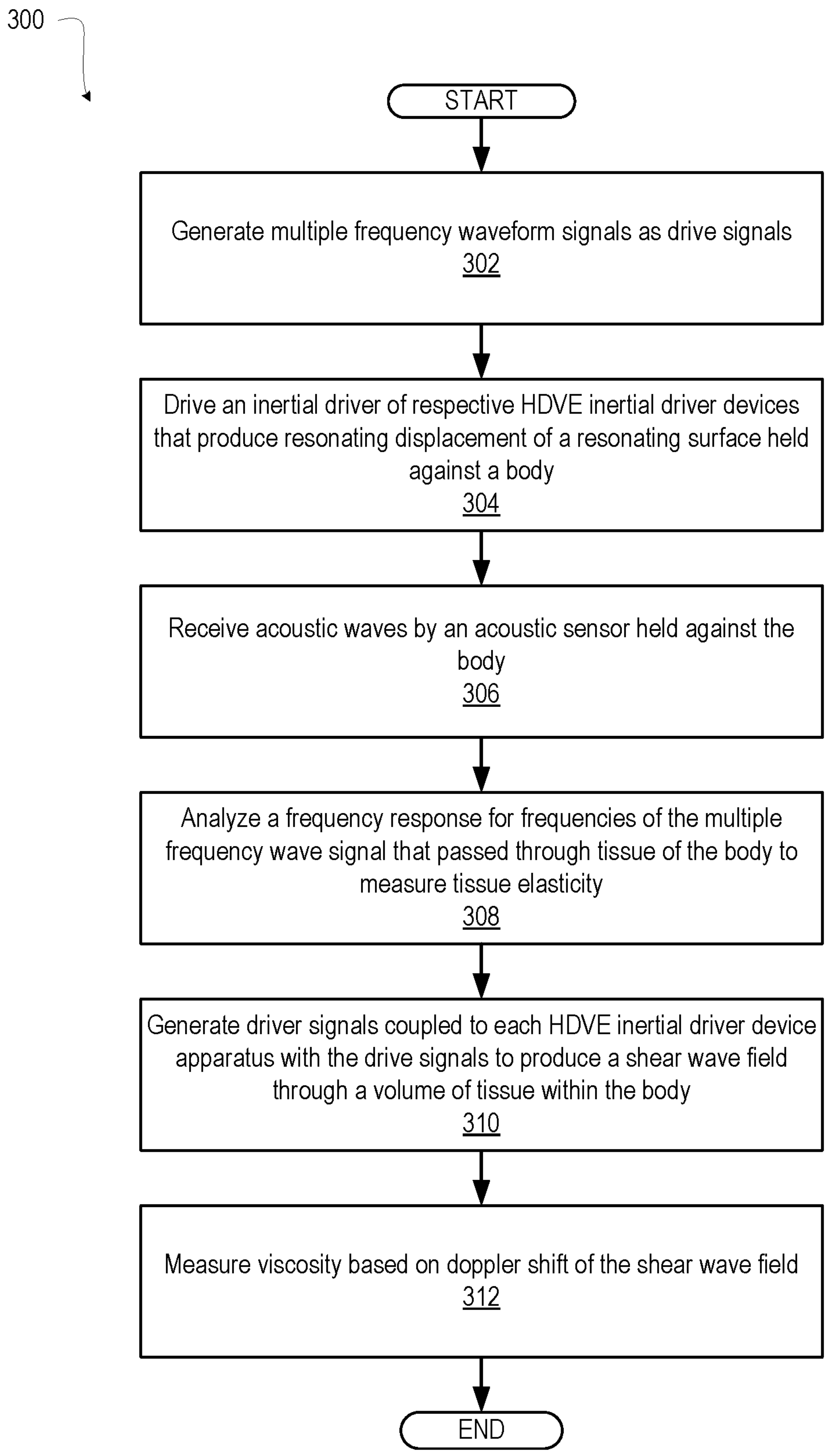
FIG. 3 is a flow diagram of a method for measuring viscoelastographic properties of tissue of a body, according to one or more embodiments.

FIG. 3 is a flow diagram of a method 300 for measuring viscoelastographic properties of tissue of a body. In one or more embodiments, method 300 includes generating multiple frequency waveform signals as drive signals (block 302). Method 300 includes driving an inertial driver of respective HDVE inertial driver devices that produce resonating displacement of a resonating surface held against a body (block 304) to induce a shear wave field through a volume of tissue within the body. Method 300 includes sending acoustic pulses and receiving acoustic echoes by an acoustic sensor held against the body (block 306). Method 300 includes analyzing the acoustic echoes to calculate tissue displacements or tissue velocities for at least one of the frequencies in the multiple frequency wave signal that passed through tissue of the body (block 308). Method 300 includes calculating shear wave speeds from the tissue displacements or velocities in the volume of tissue on at least one of the frequencies in the multiple frequency wave signal to determine stiffness, and if performed on more than one frequency, then also calculating viscosity (block 310). In one or more embodiments, the shear wave field is a selected one of: (i) crawling waves; (ii) reverberant waves; and (iii) monodirectional waves in an acoustic frequency range of 0.1 Hz to 80 kHz with power sufficient to produce a displacement in a range of 0.1 to 50 μm. Then method 300 ends.

In one or more embodiments, method 300 includes putting the body under examination on a table in skin contact with the HDVE inertial driver devices. The method 300 multiple frequency wave signal can be a chord. For example, the chord can include 10-15 discrete frequencies or more. The chord can contain hundreds of discrete frequencies or could also be white noise with all frequencies at once. In an exemplary embodiment, the frequencies occur at once so that each frequency passes through an identical region of tissue in the same conditions.

In one or more embodiments in analyzing the response, Doppler ultrasound is used to calculate tissue displacements or velocities. A selection is made of one, two or three of the following to be put on screen: (a) Display normal ultrasound output on screen (B-mode; greyscale); (b) Display normal B-mode with overlay of stiffness image as a color map; and (c) Display normal B-mode with overlay of viscosity image; or both stiffness and viscosity together are overlaid on the normal B-mode ultrasound image. Viscosity is typically calculated as function of how stiffness changes as function of frequency. In one or more embodiments, input of all three is through same input sensor, which could be inside probe. For example, the ultrasound wand pings out the ultrasound waves and then reads them through piezoelectric crystals, which can be ceramics. As waves come in, the piezoelectric crystals (or ceramics) are listening and receive ultrasound waves that bounce back (the echoes).

In one or more embodiments, the present disclosure provides for systems and methods for use with elastography and viscoelastography imaging. In one or more other embodiments, the present disclosure provides for systems and methods for utilizing acoustic vibrations for nondestructive testing and seismic mapping.

In one or more embodiments, the present disclosure provides a system for creating longitudinal, transverse and shear wave fields inside a body or object, including reverberant, crawling wave, and other shear and longitudinal wave fields, for safe, single and multi-source external HDVE inertial drivers for shear and longitudinal wave-based elastographies and viscoelastographies.

In one or more embodiment, the systems include an acoustic energy source such as an HDVE inertial driver source or sources that can generate and inject single, multiple, and arbitrary waveforms such as one with a plurality of sinusoids, triangle waves, square waves, complex waves (including noise) of a single frequency or of various frequencies, phases, and amplitudes. When one or more of these sources are placed on the body or object, independent waveforms can be injected and directed into a tissue or region of interest to create a reverberant shear wave field, a crawling wave shear wave field, or other wave fields.

In one or more embodiments, several elements are used for creating reverberant shear wave fields in humans, especially for deep penetration in larger and obese bodies. These include: (a) a plurality of sources operating above 20 Hz capable of producing at least 0.5 micrometers to 50 micrometers of displacements from shear waves within deep tissues. The sources must have high efficiency for long duration scans with minimal heating; (b) alternatively, an extended source created by incorporating a flexible element to one or two discrete sources; (c) a specially designed contact surface dome to apply on the surface near the area of interest for elastography; (d) applying at least 0.1 pound of contact force across the dome for some tissues; and (e) applying and later removing the contact force in a rapid manner to shorten the examination time and the work required by the clinician.

In one or more embodiment, the present disclosure provides for a system and method for elastography includes an HDVE inertial driver or HDVE inertial driver system configured to be positioned adjacent to an imaging subject and configured to impart mechanical energy into the tissue or material of the subject. In one or more embodiment, an external HDVE inertial driver source is included and configured to induce shear waves in a volume of tissue in the body or a volume of material in an object for use with elastography and viscoelastography.

In one or more embodiment, the present disclosure provides for an acoustic energy source external to the imaging subject that is mechanically or acoustically coupled to the member, and the distal end of the member is adapted to contact the surface of the subject. The acoustic energy coupled to the member causes at least the member to mechanically vibrate and generate shear waves within the subject. The member is preferably flexible over at least a portion to facilitate contouring to the subject.

In one or more embodiment, the member is positioned at a selected location on the subject, and detection of the generated waves is performed by imaging the shear waves generated by the member with an imager capable of resolving an image created by the waves generated. In one or more embodiment, the imager may be one or more imaging device including but not limited to ultrasound and magnetic resonance imaging (MRI).

In one or more embodiment, the acoustic energy source causes the member to vibrate longitudinally along its axis. In another embodiment, the acoustic energy source causes vibratory motion of the transducer, preferably along its axis. Those skilled in the art will appreciate that mechanical contact between the member and the surface of the subject body ensures transfer of mechanical energy to adjacent materials and the generation of shear waves.

In one or more embodiment, the system includes a controller coupled to and configured to control an acoustic actuator (tactile transducer). A member has a first end coupled to the acoustic actuator and a second end positioned adjacent to a subject material or tissue region of interest. In one embodiment, the actuator couples acoustic energy into the member, for example, by repeatedly vibrating a first end of the member. In this manner, mechanical waves caused by longitudinal vibration of the member may be projected into tissue creating shear waves.

In one or more embodiment, the system includes a controller, which may cause a frequency of the longitudinal and shear waves to be, for example, within a range of 0.1 Hz and 5000 Hz. In one or more embodiment, the system includes a controller, which may cause a frequency of the longitudinal and shear waves of at least 10, 20, 30, 40, 50, 60, 70, 80, 100, 120, 140, 160, 180 200 Hz or more. In one or more embodiment, the system includes a controller, which may cause a frequency of the longitudinal and shear waves at most 5000, 4000, 3000, 2500, 2000, 1500, 1000, 800, 600, 400, 200 Hz or less.

The controller may also be designed to pulse the vibration of the member synchronously with an imaging sequence of a medical imaging apparatus (not shown) or to continuously vibrate the member.

In one or more embodiment, the system includes a computing system, which may include a processor, data storage, and logic. These elements may be coupled by a system or bus or other mechanism. The processor may include one or more general-purpose processors and/or dedicated processors and may be configured to perform an analysis of or on the output from the system. An output interface may be configured to transmit output from the computing system to a display. The computing system may be further configured to send trigger signals to any of the acoustic actuator and signal generator. Such trigger signals may be sent by the computing system to synchronize the actuator with the signal generator.

The processor may further control the actuator, such as to turn it on or off, set sensing parameters, or provide calibration settings. An example computing device includes a processor, a memory, an input/output interface, and a communication interface. A bus provides a communication path between two or more of the components of computing device. The components are provided by way of illustration and are not limiting. Computing device may have additional or fewer components, or multiple of the same component. Processor represents one or more of a general-purpose processor, digital signal processor, microprocessor, microcontroller, application specific integrated circuit (ASIC), field programmable gate array (FPGA), other circuitry effecting processor functionality, or a combination thereof, along with associated logic and interface circuitry. Memory represents one or both of volatile and non-volatile memory for storing information (e.g., instructions and data). Examples of memory include semiconductor memory devices such as EPROM, EEPROM, flash memory, RAM, or ROM devices, magnetic media such as internal hard disks or removable disks or magnetic tape, magneto-optical disks, CD-ROM and DVD-ROM disks, holographic disks, and the like.

In another embodiment, the member includes a flexible membrane to impart waves into the tissue. In another embodiment, the system includes a function generator coupled to an audio amplifier. Audio amplifier drives an audio output device such as a loudspeaker that has been converted to an HDVE inertial driver. In another embodiment of the invention, the member comprises a flexible membrane. The membrane is coupled to audio output device. In another embodiment of the invention, the member may be fluidly and pneumatically coupled to audio output device. In another embodiment of the invention, the member includes a hollow body and an elastic or pliable membrane, which allows mechanical wave propagation. The vibratory action of membrane produces both longitudinal and shear waves, with shear waves preferentially generated at the edges of the membrane.

In another embodiment of the invention, the audio output device comprising function generator and audio amplifier induces a time-varying pneumatic pressure at one or more desired frequencies, and acoustic energy is transferred to member. Application of the time-varying pressure within member causes membrane and member to vibrate. Through vibration of membrane, longitudinal and shear waves are caused to propagate into a tissue region of interest.

In another embodiment of the invention, the function generator may cause a frequency of the longitudinal and shear waves to be, for example, within a range of 30 Hz and 3000 Hz. Function generator may also be designed to pulse the vibration of member synchronously with an imaging sequence of a medical imaging apparatus (not shown) or to continuously vibrate distal member.

Those skilled in the art will appreciate that a wide range of HDVE inertial drivers are contemplated by the invention. For example, the HDVE inertial driver may be an electromagnetic actuator, piezoelectric actuator or a pneumatic actuator converted to an HDVE inertial driver.

In one or more embodiment, the drive signal may be a sinusoidal signal with, for example, a peak voltage of 25V driven into the HDVE inertial driver from a power amplifier at frequencies within a range of 0.01 Hz and 80,000 Hz. In another embodiment, a peak voltage of 5V vibration may be produced at frequencies within a range of 30 Hz and 300 Hz. In another embodiment, the vibration may be produced at frequencies within a range of 50 Hz and 1000 Hz. The signal may be low-pass filtered with, for example, a cut-off frequency of 2 kHz, that removes high-frequency noise that might interfere with imaging. The signal may be generated in burst or pulsed mode and is preferably controlled such that the imaging is synchronized with vibration. A continuous signal may instead be generated if desired.

In another embodiment, the system includes a digital signal processor, which transmits the signal through a secondary amplifier, which transmits the signal, preferably unfiltered, to the HDVE Inertial Driver Apparatus.

In one embodiment, an electroactive transducer has at least one integral active feedback control loop and at least one integral amplifier. The electroactive transducer may include one or more of a position sensor, orientation sensor, force sensor, load sensor, temperature sensor, pressure sensor, proximity sensor, optical sensor electrical sensor, and/or magnetic sensor; and input from at least on of such sensors can be used to control at least one signal to an amplifier so as to control the frequency response of one or more HDVE Inertial Drivers.

In some embodiments, an HDVE Inertial Driver arrangement may be incorporated into a wearable device. The device may be a separate unit that is placed against a user's body or is incorporated into clothing or articles that are worn on the body or are positioned against the body. The HDVE Inertial Driver may therefore be incorporated into any type of wearable article including but not limited to a backpack, a vest, a body-suit, a jacket or any other garment or piece of clothing.

In one embodiment, an HDVE Inertial Driver includes an active feedback control loop and an amplifier. The active feedback control loop may be integrated with an HDVE Inertial Driver arrangement. Furthermore, the amplifier may be integral with the HDVE Inertial Driver in that the amplifier and HDVE Inertial Driver may be in close proximity, including being integrated into a single unit. The active feedback control loop may include one or more sensors that are operatively connected to the amplifier; for example, wherein outputs from one or more sensors may be used as input(s) for one or more subsequent processes such as for example, they may be used to control at least one signal to an amplifier which provides an output electrical signal suitable to control at least one HDVE Inertial Driver in order to provide an optimal frequency response and/or other characteristics, as determined by such active feedback control loop.

In some embodiments, a system is disclosed for providing optimal frequency response in an HDVE Inertial Driver comprising a feedback control DSP (i.e., a feedback control Digital Signal Processor); a Digital Analog Converter (DAC); an amplifier; an HDVE Inertial Driver; and a sensor operatively engaged with the HDVE Inertial Driver and with the feedback control DSP; and wherein input from the sensor controls at least one signal to an amplifier and thereby controls the frequency response of the HDVE Inertial Driver. In some embodiments, the sensors may include an accelerometer. An optimal frequency response may also be based on a relationship between frequency and intensity that is based on boosting or attenuating certain parts of the frequency spectrum.

In some embodiments, a control system may configure differing sensors (and/or sets thereof) for differing sample rates and frequencies of communication with such control systems. Some sensors may employ one or more algorithms that act upon the incoming raw sensor data to produce, for example, an average, Max-Min, Poisson distribution or other processed output suitable for communication to one or more control systems.

In one embodiment, an HDVE Inertial Driver comprises a transducer to convert an electrical signal into motion. One or more membranes are coupled to the HDVE Inertial Driver. The one or more membranes transfer vibrations from the HDVE Inertial Driver to a user's body. A first sensor monitors the vibrations of the HDVE Inertial Driver. One or more circuits generate the electrical signal based on a signal received from the first sensor that monitors the vibrations of the HDVE Inertial Driver.

In one embodiment, the one or more circuits comprise a digital signal processor (DSP) to receive an audio input signal and the signal from the first sensor, the DSP processing the audio input signal to generate a modified signal based on the signal from the first sensor; a digital to analog converter (DAC) to convert the modified signal into an analog signal; and an amplifier to amplify the analog signal to generate the electrical signal for the HDVE Inertial Driver.

In one embodiment, the HDVE Inertial Driver includes an enclosure, and the first sensor and the amplifier are located within the enclosure. In one embodiment, the first sensor is embedded within the one or more membranes. In one embodiment, the one or more circuits adjust an equalization of the electrical signal based on the signal received from the first sensor. In one embodiment, the one or more circuits compare a desired frequency response with a frequency response of the vibrations as indicated by the signal received from the first sensor and adjust the equalization of the electrical signal based on the comparison. One or more pressure sensors may be embedded in, for example, a membrane, ideally the membrane in direct contact with a user, such that the relative pressure of the user to such membrane may be measured. This measurement may be used to calculate the relative position of the user to the membrane.

In some embodiments many types of sensors may be deployed to provide information sets in the form of sensor output signals that may be processed by one or more DSP's in an active feedback system. The following non-limiting examples are described below.

The sensors may be accelerometers that are used to capture vibration levels and to generate an output signal indicative of the captured vibration levels. The captured vibration levels are used for initialization and configuration of DSP and/or for monitoring of output of HDVE Inertial Drivers to optimize and/or customize frequency characteristics for the application. An accelerometer may be used to detect vibrations in certain frequency bands in order to adjust response of feedback system for protection or enhancement. For example, an accelerometer embedded in the system can be used to detect vibrations in a known frequency band correlated with one or more certain failure modes. The active feedback system may then adjust, limit or stop the response according to the criticality of measurement.

The sensors may be physical or magnetic position sensors such as accelerometers, Hall effect sensors, orientation sensors such as gyroscopes or mercury tilt switches, electrical or mechanical pressure sensors, optical sensors such as photodiodes or photoresistors. The sensors may be used individually or in combination with other sensors for monitoring or detecting a change in a user's position or orientation relative to a previous state. This system for monitoring or detecting a change in user's position or orientation may comprise a combination of these sensors and/or may form an array of these sensors so as to detect the change in position of a user in relation to an HDVE Inertial Driver arrangement. These sensors or sensor arrays may be used to initialize and configure a user and/or HDVE Inertial Driver arrangement position in relation to an environment and/or each other.

A pressure sensor, which in some embodiments may include combinations of other sensors, for example force and load sensors, may provide a sensor output signal indicative of an amount of pressure being applied by a user to the HDVE Inertial Driver apparatus. This information can be used for the initialization and configuration of an HDVE Inertial Driver arrangement. This information may also be used for detecting presence of a user and for varying (including muting) an output if the user is not present. This may include the relative and absolute positioning of an HDVE Inertial Driver arrangement that is worn by a user and/or against which a user sits, for example in a bed or chair.

A proximity sensor may employ, for example photo resistors and or optical or IR LEDS so as to determine the reflections/refractions of optical and/or IR wavelengths, so as to determine the proximity of a user to an HDVE Inertial Driver arrangement and to generate a sensor output signal indicative of this proximity. For example, such a sensor may be placed in a bed or seat back and in a wearable transducer arrangement so as to determine variation in distance of user to bed or seat, for example, to determine if the user is arching his or her back off the bed, or leaning forward in a seat, and is thus less connected to the HDVE Inertial Driver array. In this example, the DSP may increase the output of the HDVE Inertial Driver arrangement so as to maintain a constant amplitude of the signal as perceived by a user and/or may increase or decrease the amplitude to specific transducers in an HDVE Inertial Driver arrangement, for example increasing the amplitude on one side of the bed or in the base of the seat, whilst reducing amplitude on the other side of the bed or in the seat back, where such a bed or seat is fitted with such an HDVE Inertial Driver arrangement.

A back EMF (electro-magnetic field) sensor may be used to sense the operation of one or more HDVE Inertial Driver in an HDVE Inertial Driver arrangement, for example producing a PWM (Pulse Width Modulated) output that may be supplied to a DSP. Such a signal may be used for both protection of the HDVE Inertial Driver arrangement though maintaining operations of the HDVE Inertial Drivers arrangement in a safe operating zone and/or for optimization and/or variance of the signal so as to provide a user with the appropriate shear wave fields.

Various sensors can be used to measure vibrations of an HDVE Inertial Driver. For example, an accelerometer may be used to measure force or acceleration of an HDVE Inertial Driver. A magnetometer may be used to measure the magnetic flux and thus force of an HDVE Inertial Driver. A galvanic skin response sensor (e.g. EKG) may provide physiologic information sets that may be made available to DSP so as to optimize a user's engagement with the vibration field provided by an HDVE Inertial Driver arrangement.

A temperature sensor may be either be a contact or non-contact type sensor. Temperature sensors include, but are not limited to, the following example types which may be employed to monitor the temperature of an HDVE Inertial Driver arrangement and/or the components thereof, including supporting components such as amplifiers. A thermocouple or a thermopile may be used to monitor temperature of the HDVE Inertial Driver elements, electrical elements or any functional or cosmetic enclosures. If a critical limit is exceeded, for example a temperature that could cause damage to the components, or a temperature that would be uncomfortable for a user, the DSP can reduce the amplitude of it output or complete mute its output. Examples of temperature sensors include thermostats, thermistors, resistive temperature detectors and thermocouples.

A DSP processor may form part of an active feedback system. A DSP processor or processors may be integral to the unit and/or be external to the unit, connected wired or wirelessly in proximity to the device or remotely over a network. The DSP processor acts to accept input from one or more sensors, evaluate such input and undertake one or more actions based on this input. The DSP may have a repository of sensor input samples which are representative of specific operating circumstances of an HDVE Inertial Driver arrangement. For example, this may include the response of the sensors with an HDVE Inertial Driver arrangement aligned vertically or horizontally. In some embodiments, this may include one or more patterns created by one or more sensors that represent an optimum frequency response or other vibration characteristics as measured by such sensors, or other sensors and/or selected by a user. The DSP may store information such as the following and not limited to: sensor inputs and measurements, calculations and correlations of measurements, critical measurements, critical faults and frequency of critical faults, corrections and enhancements performed for certain conditions, and general state of system or certain subsystems. The DSP processor may also communicate such information to subsystems or to external systems locally or over a network. The DSP may also receive configuration information, updated settings or system state settings from subsystems or external systems locally or over a network.

The DSP may initiate processes to modify the incoming vibration signal so as to create an output signal that when fed to an amplifier connected to an HDVE Inertial Driver arrangement may produce an optimized and/or specific frequency response or other vibration characteristics.

The DSP processes may include filtering (notch, high, low, multi band, bandpass and the like) with varying rates of Q (the steepness of the filter), for example to remove a specific resonance caused by, for example a bed, seat or other environmental artifacts. DSP may employ a range of algorithms to vary signals fed to amplifiers. Such algorithms may be deployed through, for example analysis of the input signal and/or analysis of the sensor output signals. The DSP may also monitor the output of amplifier to further adjust for any discrepancies caused by operations of amplifier. Other processes may include limiting the output vibration signal to reduce transients and other peaks, compressing the vibration signal to reduce overall dynamic range and produce a more consistent operating level. Other processes can include phase alignment of the output vibration such that the vibration signal is aligned with potentially other vibration signals, for example those from other independently driven HDVE Inertial Drivers, and the like.

The DSP may also act to attenuate the output signal and in some cases remove the output completely, generally in response to inputs from and evaluation of such information from those sensors that are protecting the HDVE Inertial Drivers, for example accelerometer and temperature sensors, where the rate of acceleration may exceed or indicate that an HDVE Inertial Driver will exceed the safe operating environment for an HDVE Inertial Driver and/or temperature measurements which indicate, for example that the coils of the HDVE Inertial Driver(s) are generating heat in excess of safe operating conditions. The DSP may, in some embodiments correlate multiple sensor inputs to avoid false positives and/or to compare such inputs with stored values so as to determine in advance of exceeding one or more thresholds an appropriate variation of the output signal to avoid a failure state.

The DSP may have an initial configuration state, whereby the DSP generates specific vibration signals and then employs the sensors to measure such signals so as to create an optimum vibration output for a specific HDVE Inertial Driver arrangement for one or more organs or tissues in the patient or object. Such configurations may be stored by DSP and may generate modifications to an input signal so as to create an output signal with characteristics that optimize the vibration field for a patient or object. In some embodiments, this may involve the DSP providing instructions to a patient or object, through for example tactile sensations, such as creating an impulse from a specific point of a membrane, for example the left side, which informs the patient or object to lean on that left side, so that their body position relative to the membrane may be determined and the output signal adjusted for optimum vibration response. For example, one impulse may mean lean into the membrane, two pulses mean lean out, and three pulses mean configuration complete. A DSP processor may also be configured to accept an incoming vibration signal and process that signal such that the HDVE Inertial Driver arrangement is provided with the appropriate frequencies.

FIGS. 4-19 illustrate several embodiments of the present innovation and its details. Those skilled in the art will appreciate that the invention can inject multiple sinusoids serially or simultaneously of various frequencies, phases, and amplitudes, as well as random noises, single sinusoids, complex audio waveforms, and other arbitrary waveforms into the body or object. Thus, the present invention can be used for a variety of applications, including many forms of elastography and visco-elastography, crawling wave elastography, reverberant elastography, and others.

Figure 4:
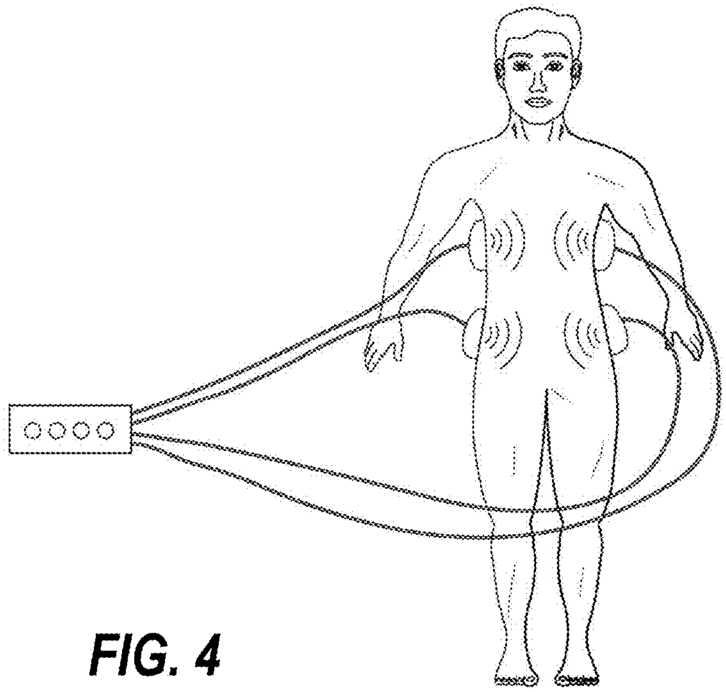
FIG. 4 illustrates a system using four HDVE inertial drivers (sources), according to one or more embodiments, shown here generating a reverberant field.

FIG. 4 illustrates a system to generate a reverberant field in a body using four HDVE Inertial Drivers (sources) coupled to the body and driven by a multichannel amplifier using multi-channel audio inputs, a power source (e.g., AC or battery), all connected via electrical communications, according to one or more embodiments. In one embodiment, the electrical communications consist of an AC power cord, audio cables, and standard loudspeaker cables. Those practiced in the art will appreciate that some of these communications can be wireless and/or powered with batteries. This setup also enables Reverberant Shear Wave Fields, Crawling Wave Fields, as well as other useful fields to be generated in the patient or object. In this illustration, "tactile audio transducers" and "electro-mechanical vibration drivers" means HDVE Inertial Drivers.

Figure 5:
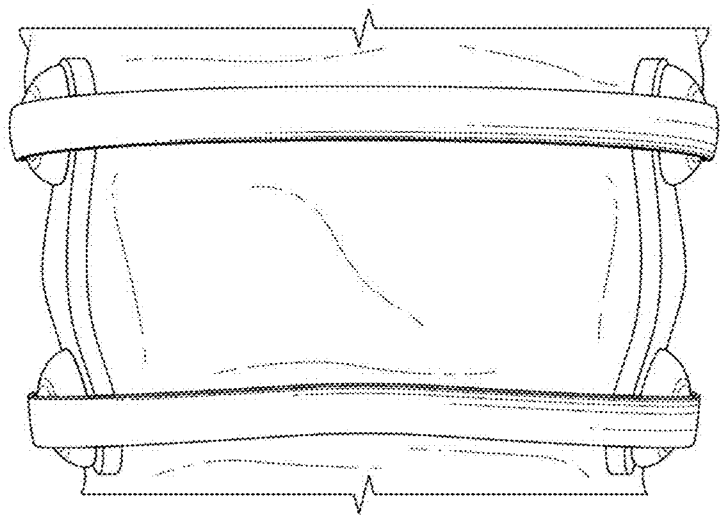
FIG. 5 illustrates a harness, according to one or more embodiments, to hold HDVE inertial drivers in FIG. 2 against the body or object.
Figure 6:
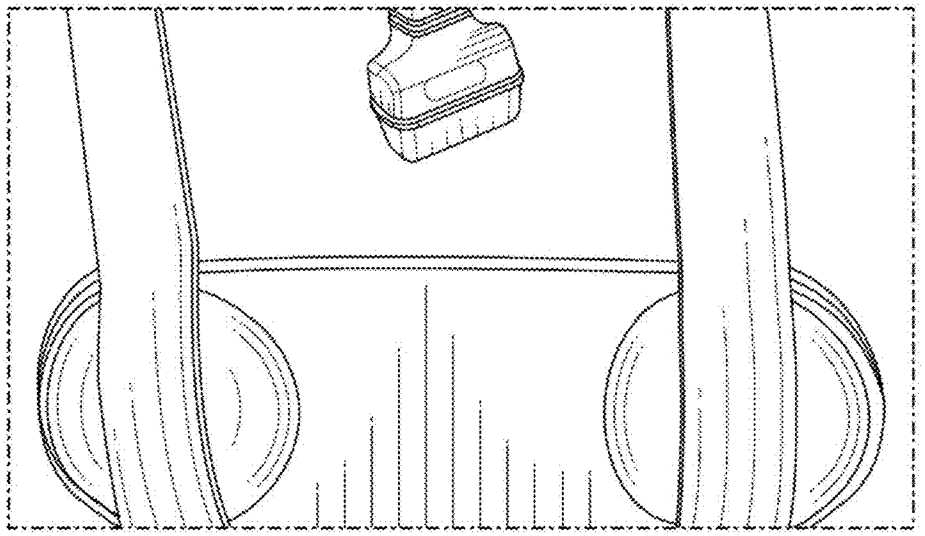
FIG. 6 illustrates a harness, according to one or more embodiments, which allows HDVE inertial drivers to be placed where needed on the body or object, in this case, near an ultrasound probe's imaging site.

FIG. 5 illustrates a harness, according to one or more embodiments, to hold HDVE Inertial Drivers in FIG. 4 against the body or object;

FIG. 6 illustrates a harness, according to one or more embodiments, which allows HDVE Inertial Drivers to be placed where needed on the body or object, in this case, near an ultrasound probe's imaging site.

Figure 7:
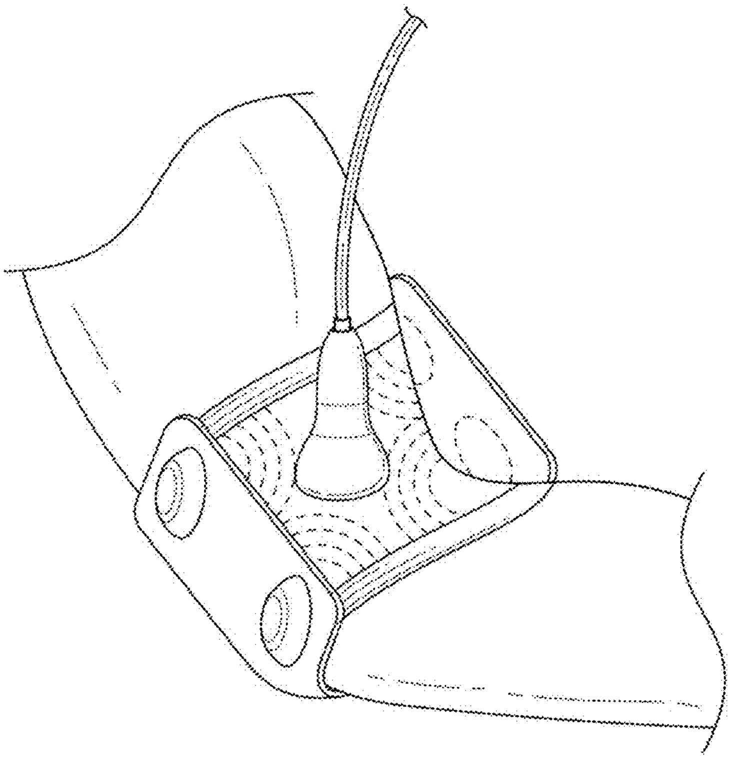
FIG. 7 illustrates a harness system for a leg, arm, neck, or similar body part or object, according to one or more embodiments, shown here generating a reverberant field.

FIG. 7 illustrates a harness system, according to one or more embodiments, to generate a Reverberant Shear Wave Fields (illustrated), Crawling Wave Fields (not illustrated), or other useful fields in a limb or neck or child's torso for use with ultrasound imaging. In this illustration, "tactile audio transducers" and "electro-mechanical vibration drivers" means HDVE Inertial Drivers.

Figure 8:
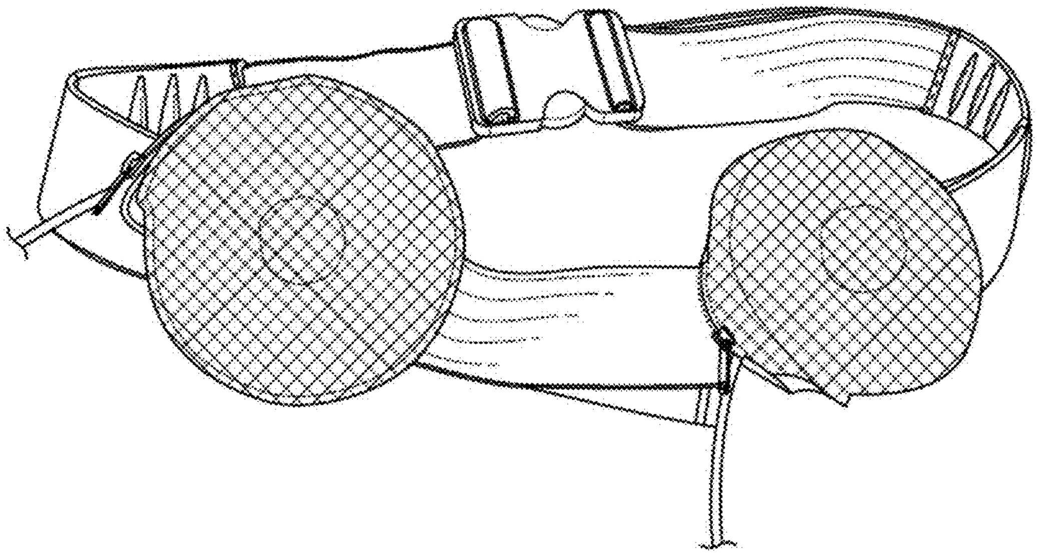
FIGS. 8-10 illustrate an adaptable harness system, according to one or more embodiments.
Figure 9:
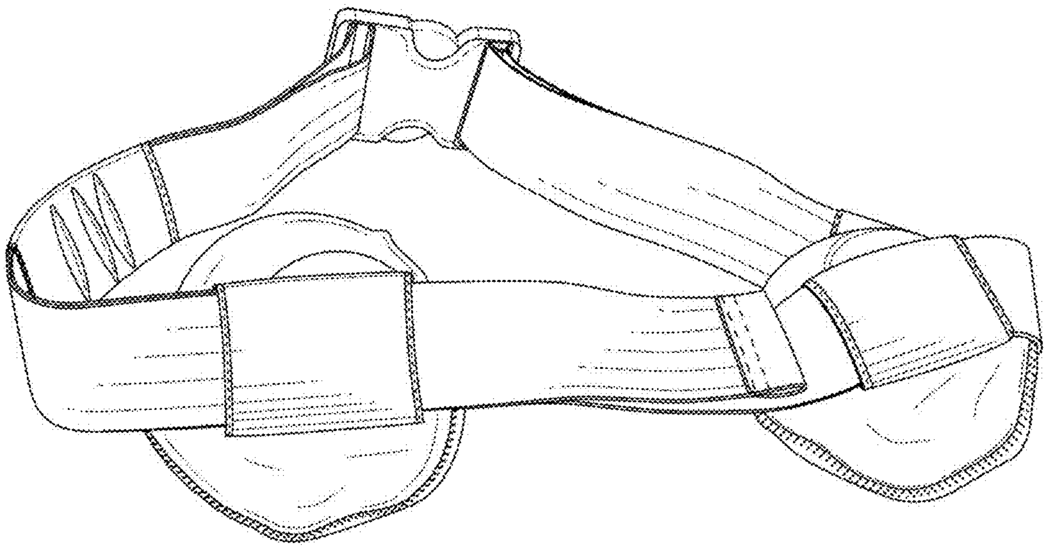
Figure 10:
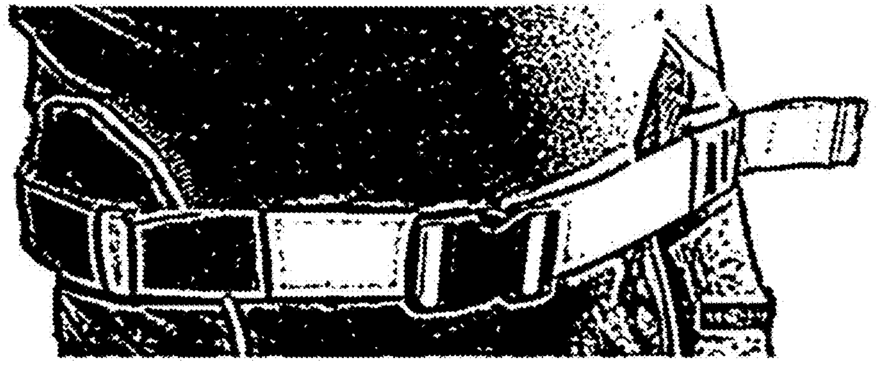

FIGS. 8-10 illustrates an adaptable harness system, according to one or more embodiments, to position and hold HDVE Inertial Drivers against the body or object. FIG. 8 is a picture of a harness showing the harness straps, quick connect fasteners for easy on-off and adjustable strap length, and the body contact surface of harness pocket holding the HDVE Inertial Driver. FIG. 9 is a picture of the same harness, showing outside surface (non-contact surface) of the harness pocket. FIG. 10 is a picture of the harness system attached to a body.

Figure 11:
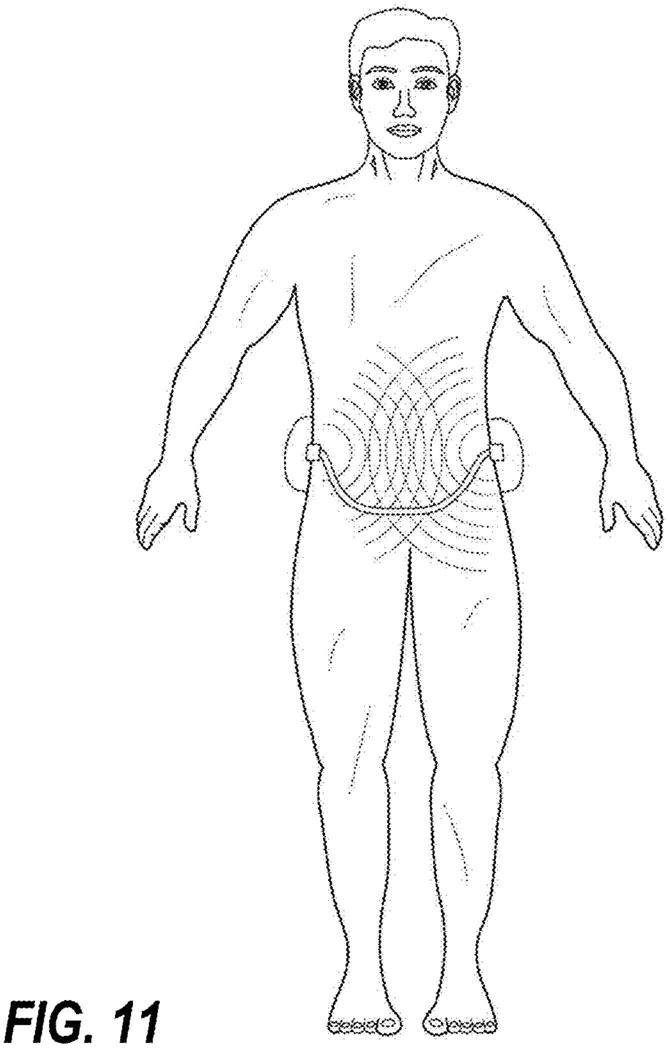
FIG. 11 illustrates a spring bar "head-phone style" system to hold HDVE inertial drivers against a body without obstructing the exam field, according to one or more embodiments, shown here generating a reverberant field.

FIG. 11 illustrates a spring bar "head-phone style" system, according to one or more embodiments, to position and hold HDVE Inertial Drivers against the body or object for quick on-off, with and without supplemental straps, to generate Reverberant Shear Wave Fields (illustrated), Crawling Wave Fields (not illustrated), or other useful fields. Illustrated is the front view of a spring bar with offset to allow positioning of the HDVE Inertial Drivers without interfering with or physically blocking the zone or region where the ultrasound probe will be placed. Not shown in this particular illustration is an optional strap around the backside of the patient. This style will have application to torso, leg, arm, and neck in obese and non-obese adults, children, infants, and other objects. In this illustration, "audio transducer" and "electro-mechanical vibration driver" means HDVE Inertial Drivers.

Figure 12:
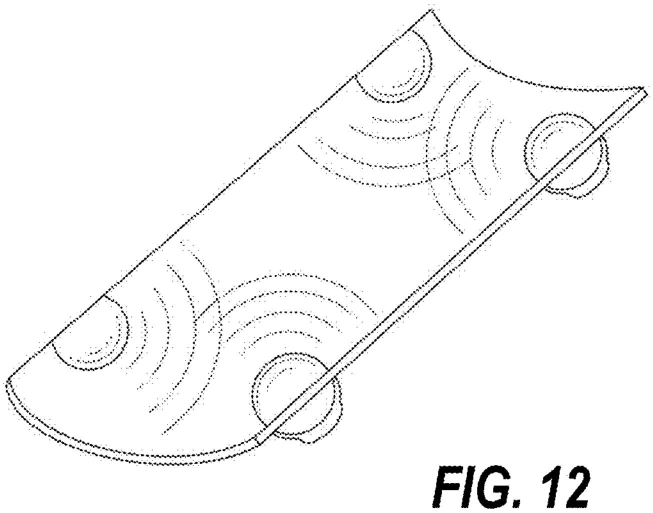
FIG. 12 illustrates a mat with embedded HDVE Inertial drivers, according to one or more embodiments, shown here generating a reverberant field.

FIG. 12 illustrates a mat with embedded HDVE Inertial Drivers, according to one or more embodiments, to generate a Reverberant, Crawling Wave, or other useful wave field. Patient simply lies on the mat or object is placed on the mat. Such a system could contain a multitude of HDVE Inertial Drivers. In this illustration, "audio transducers" and "electro-mechanical vibration drivers" means HDVE Inertial Drivers.

Figure 13:
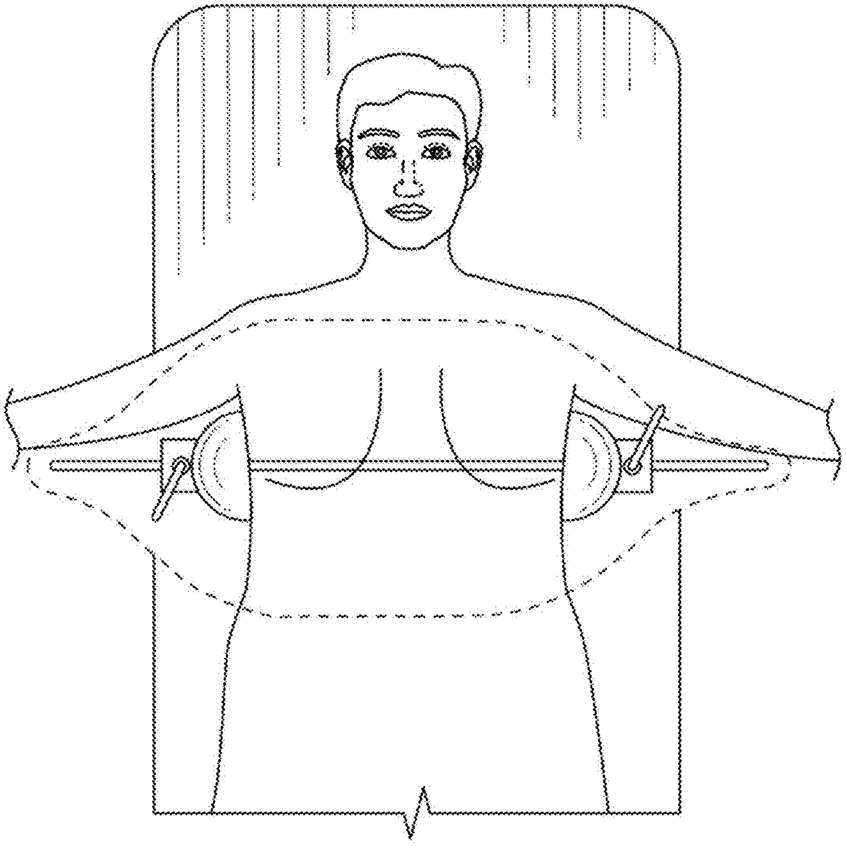
FIG. 13 illustrates a pad with sliding channel for adjusting placement of HDVE inertial drivers in communication with a patient contact dome, according to one or more embodiments.

FIG. 13 illustrates a pad with sliding channel for adjusting placement of HDVE Inertial Drivers including patient contact domes, according to one or more embodiments, for which the drivers can be quickly positioned against the ribs, hips or other body parts, and driven simultaneously (for example, one set against the ribs and a second set against the hips, as well as other combinations). In one application, multiple systems are utilized wherein one of the systems is placed crosswise on the table near the ribs, and a second system is placed crosswise on the table near the hips; the patient then lies on top of them, and the HDVE Inertial Drivers are moved along the channels from both sides towards the patient until each driver dome contacts the patient with a desired angle and force.

Figure 14:
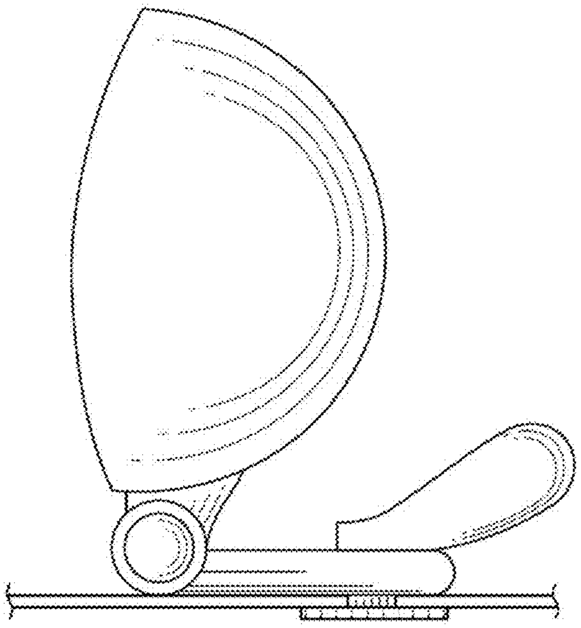
FIG. 14 illustrates the sliding channel HDVE inertial driver system in FIG. 13, according to one or more embodiments.

FIG. 14 illustrates the sliding channel HDVE Inertial Driver system in FIG. 13, according to one or more embodiments, having a quick-lock driver apparatus. Hinge with spring (metal or plastic), elastomer, or flexing arm, enables adjustment of patient contact force.

Figure 15:
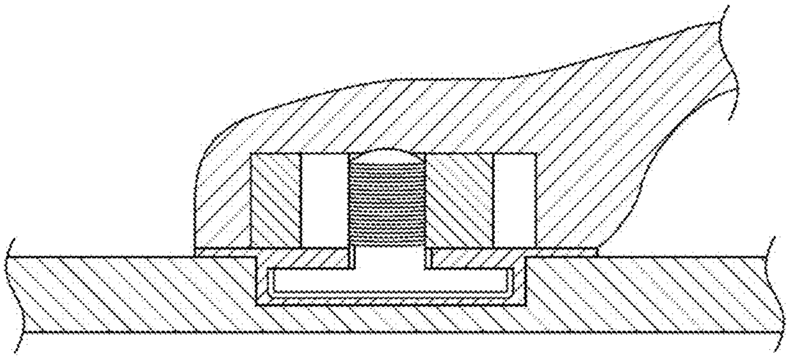
FIG. 15 illustrates the Threaded T-lock for sliding channel system in FIG. 14, according to one or more embodiments.

FIG. 15 illustrates the Threaded T-lock, according to one or more embodiments, for sliding channel HDVE Inertial Driver system in FIG. 14.

Figure 16:
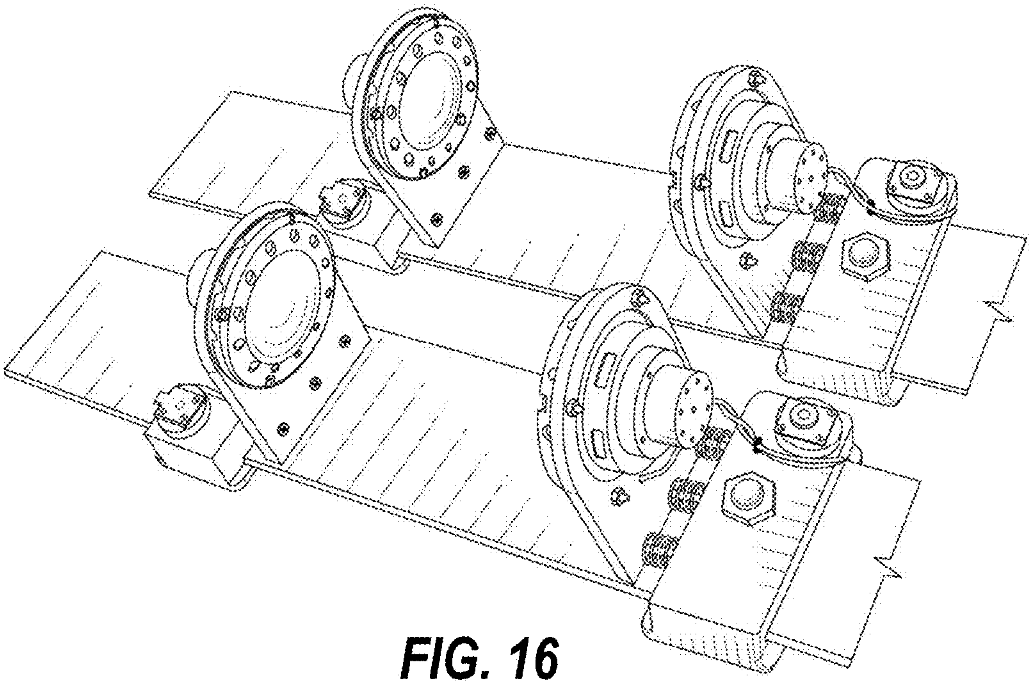
FIG. 16 illustrates an embodiment with two sliding track electro-mechanical vibration systems, according to one or more embodiments.

FIG. 16 illustrates an embodiment with two sliding track HDVE Inertial Driver systems (two identical systems shown). Flexible arm hinge with three metal springs each enables setting of patient contact angle and force.

Figure 17:
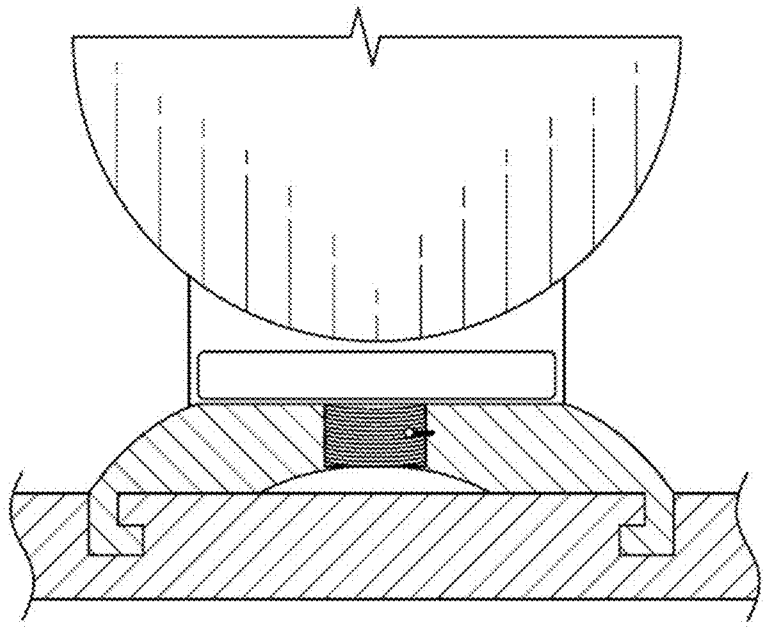
FIG. 17 illustrates a pressure lock, according to one or more embodiments.

FIG. 17 illustrates a pressure lock, according to one or more embodiments, for sliding track HDVE Inertial Driver system. In this illustration, "transducer" and "electro-mechanical vibration driver" means HDVE Inertial Driver.

Figure 18:
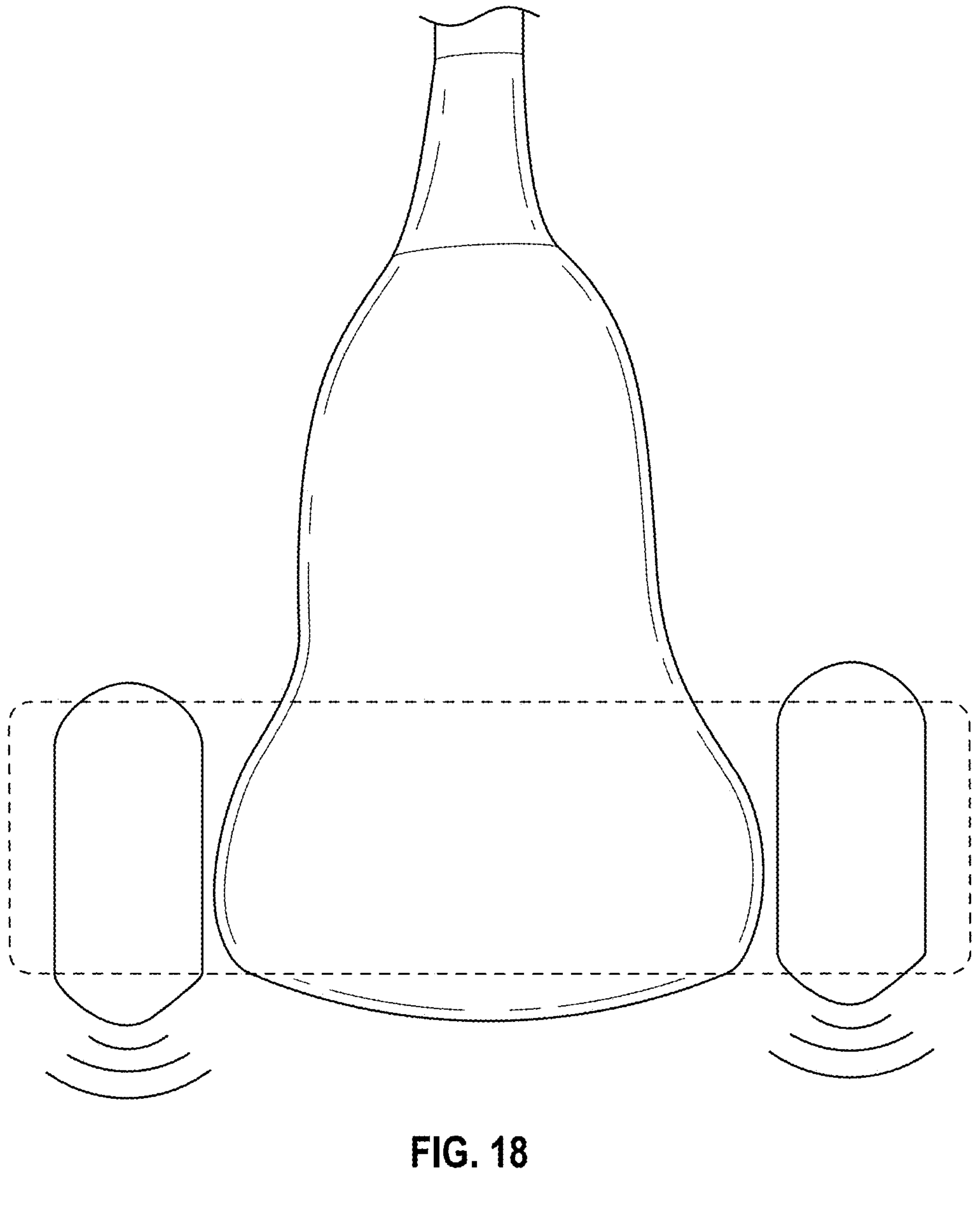
FIG. 18 illustrates HDVE inertial drivers, integrated with an ultrasound probe, according to one or more embodiments.

FIG. 18 illustrates HDVE Inertial Drivers, according to one or more embodiments, integrated with an ultrasound probe. In this illustration, by "rubber mounting" we mean "vibration dampening viscoelastic material" such as a synthetic viscoelastic urethane polymer. In this illustration, by "transducer" and "electro-mechanical vibration driver", we mean HDVE Inertial Driver.

Figure 19:
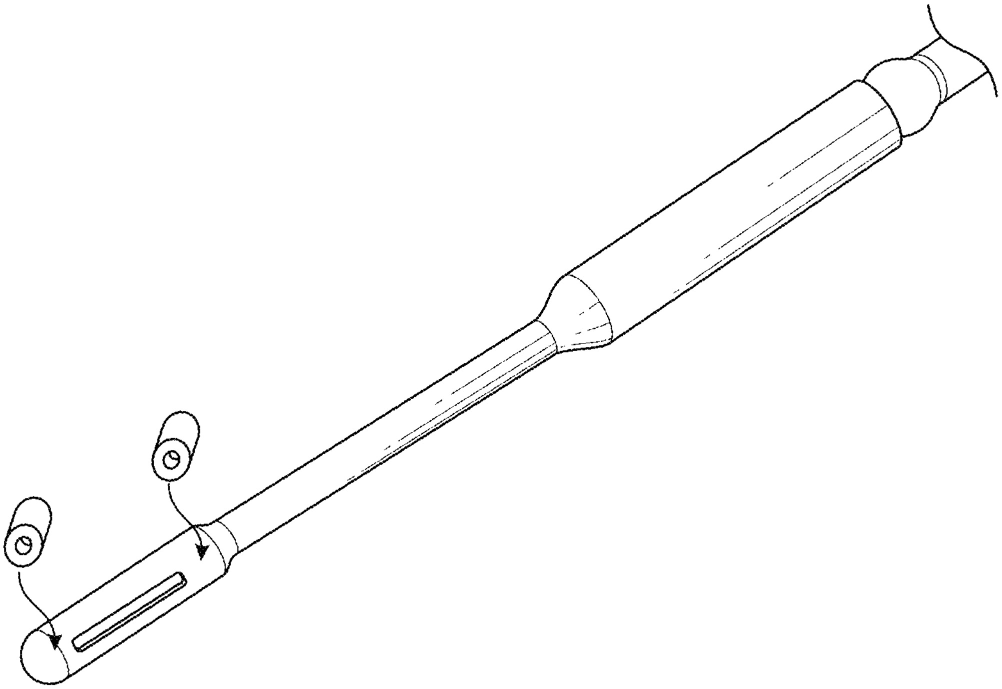
FIG. 19 illustrates miniature higher frequency HDVE inertial drivers integrated with an ultrasound transrectal probe as part of a system that can also include lower and mid-frequency HDVE inertial drivers applied to the body's external surface (not shown), according to one or more embodiments.

FIG. 19 illustrates miniature HDVE Inertial Drivers integrated with an ultrasound transrectal probe, according to one or more embodiments. Drivers are embedded on either side of the ultrasound transducer array. In one or more embodiments, the system may be configured for a transesophageal echo (TEE) ultrasound probe.

Figure 20:
FIG. 20 illustrates the overall flow diagram of signal sources and their transduction into mechanical shear waves within the body or object to be scanned, according to one or more embodiments.

FIG. 20 illustrates the overall flow diagram of signal sources and their transduction into physical vibrations within the patient or material to be scanned.

Figure 21:
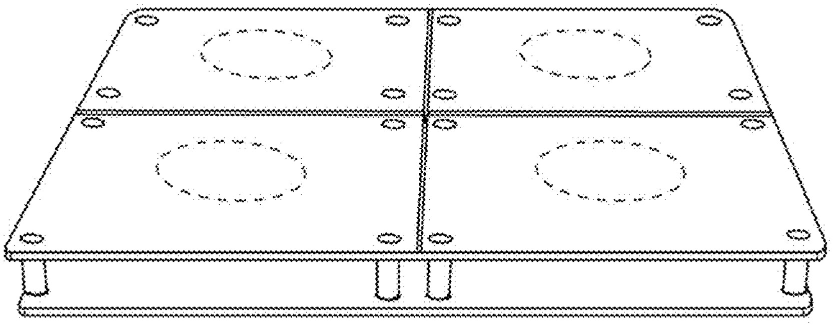
FIG. 21 illustrates another embodiment comprising a multichannel quad resonator board, according to one or more embodiments.

FIG. 21 illustrates another embodiment comprising a multichannel quadro resonator board having four HDVE Inertial Drivers arranged in an array of four top plates connected to each other with a flexible joint and each top plate connected to a single common solid bottom plate or table by steel springs.

The multichannel quadro resonator board is a vibration board with 1 to multiple HDVE Inertial Drivers, consisting of multiple contact panels connected by flexible (rubber, silicone or other material) joints, with each panel independently suspended by steel springs. In one or more embodiments, having multiple panels enables the system to drive each panel independently, allowing for complex patterns of mono, stereo and multichannel vibration distribution. The multichannel vibration distribution may include such effects as: panning, phase shifting, heterodyning and other forms of audio reproduction patterns. The multichannel quadro resonator board is designed to be used with the human body for medical imaging techniques such as reverberant and crawling wave elastography imaging, and for use with imaging other materials such as viscoelastic liquids and solids.

Figure 22:
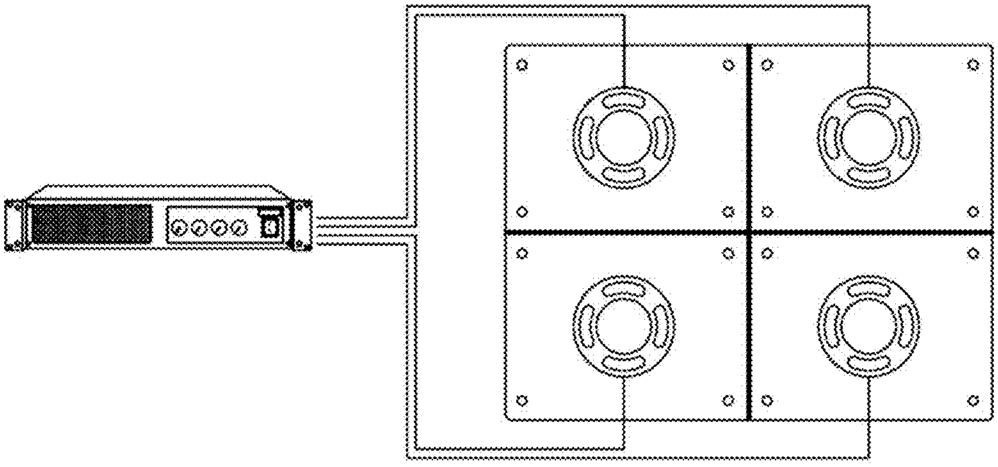
FIG. 22 illustrates another embodiment comprising a multichannel quad resonator board connected to a multichannel amplifier, according to one or more embodiments.

FIG. 22 illustrates another embodiment comprising a multichannel quadro resonator board having four HDVE Inertial Driver plates arranged in an array of four top plates wherein each driver is connected to a multi-channel audio-amplifier by electrical connection (wire). The multi-channel audio-amplifier receives input from multiple audio signal sources.

In one or more embodiments, the multichannel quadro resonator board system is scalable and may include from one plate up to 2, 3, 4, 5, 6, 7, 8, 9, 10, or more plates. In one or more embodiments, the multichannel quadro resonator board system is used for live patient use and comprises two drivers per plate.

In one or more embodiments, the multichannel quadro resonator board system comprises two or more plates wherein each plate would have its own HDVE Inertial Driver(s), and could include 1, 2, 3, 4 or more HDVE Inertial Drivers per plate, and 1, 2, 3, 4 or more plates per system, depending on application.

In one or more embodiments, the multichannel quadro resonator board system is used for the entire body and comprises 10, 12, 14, 16, 18, 20 or more independent plates.

In one or more embodiments, the multichannel quadro resonator board system comprises two or more plates forming an HDVE Inertial Driver enclosure, which may incorporate multiple drivers. In some embodiments, HDVE Inertial Drivers may be embedded in a flexible material. In some embodiments, an enclosure may be made of materials, such as metal that are suitable for the dispersion of heat generated by HDVE Inertial Drivers and associated components. Such metals include metals such as aluminum, steel, copper and the like. These may be combined with other materials that have heat dispersion properties, such as ceramics, polymers, carbon fibers composites, wood and natural fiber composites, semiconductor and the like. Enclosures may also incorporate mounting capabilities that enable them to be attached to wearable clothing, seats, couches and other artifacts. Enclosures may be rigid or flexible depending on their application.

Without wishing to be bound by theory, it is believed that the jointed nature of the resonator board comprising springs, bands or other tensioning devices, with the ability to run each quad independently or in coordination with the others for generating a plethora of shear wave fields (including crawling waves, reverberant waves, primarily monodirectional waves, etc.) at amplitudes and frequencies that other embodiments have difficulty reaching. The present invention solves various known issues in the industry including frequency range and heat problems, as the present system can generate a larger range of frequencies and safely wick heat away from the patient, as needed. In addition, the present invention provides for easy placement onto the examination or surgical table, the system is easily extensible to include supplementary HDVE Inertial Drivers on elastic belts or fabrics so as to place added vibration over a specific body part of the patient. The systems of the present invention safely route the cables and provide adequate room for driver circuitry, if needed. In addition, the systems of the present invention can also be adapted to provide multiple patient contact points (e.g., multiple protrusions of various shapes can be included in one or more embodiments).

In one or more embodiments, the multichannel quadro resonator board system may have an amplifier system that is set at a power output of less than 90, 80, 70, 60, 50, 40, 30, 20 percent of maximum nominal power output or less in order to avoid clipping of the output signal. In one or more embodiments, the multichannel quadro resonator board system amplifier may be equalized in order to provide a flat output response. In one or more embodiments, the multichannel quadro resonator board system may further comprise a power limiting in the DSP, which makes clipping not possible.

In one or more embodiments, the multichannel quadro resonator board system may further comprise a fabric design with cushions for head and feet, and mats below and/or above the multichannel quadro resonator board. In one or more embodiments, the multichannel quadro resonator board system holds the resonator board and cushions and allows the system to be folded up (like a tri-fold wallet) for transporting.

In one or more embodiments, the HDVE Inertial Driver system in the multichannel quadro resonator board system may contain vibration transducers such as those provided by MISCO, AURA, Clark Synthesis, Tectonic Elements, Dayton Audio, Visaton, Vidsonic, Guitammer, etc.

In one or more embodiments, the multichannel quadro resonator board system may further comprise an active equalization (EQ) system wherein, for example, when a 400-pound person lays down on this board, the EQ settings automatically adjust or select a preset EQ setting to accommodate the added weight so the board remains acoustically neutral (flat). In one or more embodiments, the multichannel quadro resonator board system may further comprise an accelerometer in the board and feedback to the DSP to actively control the EQ of the board.

Figure 23:
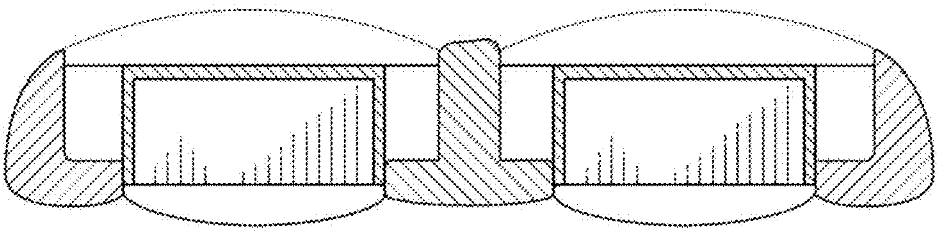
FIG. 23 illustrates another embodiment comprising a weighted HDVE inertial driver system for a tissue near the body's surface such as a breast wherein one or more weighted HDVE inertial driver systems are located adjacent to the tissue without obstructing the exam field, according to one or more embodiments.
Figure 24:
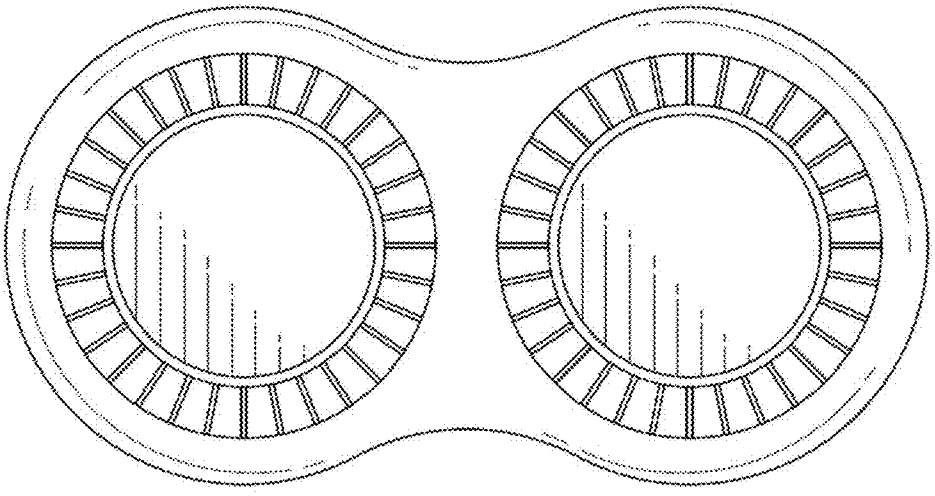
FIG. 24 illustrates an embodiment of the weighted HDVE inertial driver system of FIG. 23 in which the HDVE inertial driver system is comprised of a loudspeaker embedded in a housing that contacts the patient skin to create a sealed air column between the loudspeaker cone and the patient's skin, and which separates the loudspeaker cone and patient's skin, according to one or more embodiments.

FIG. 23 illustrates another embodiment comprising a weighted HDVE inertial driver system for a tissue near the body's surface such as a breast wherein one or more weighted HDVE inertial driver systems are located adjacent to the tissue without obstructing the exam field, according to one or more embodiments; and FIGS. 24-25 illustrate an embodiment of the weighted HDVE inertial driver system of FIG. 23 in which the HDVE inertial driver system is comprised of a loudspeaker embedded in a housing that contacts the patient skin to create a sealed air column between the loudspeaker cone and the patient's skin, and which separates the loudspeaker cone and patient's skin, according to one or more embodiments. In one or more embodiments, an apparatus is provided for transmitting selected and variable waveforms to induce shear waves in a body or object for use in elastography and viscoelastography measurement or imaging comprising: (a) one or more HDVE Inertial Drivers capable of transducing and reproducing the electrical signal to physical vibration, the HDVE Inertial Driver being mounted to a housing that physically contacts the body or object, for inducing shear waves of selected frequencies and amplitudes as well as arbitrary complex waveforms such as sine waves, square waves, triangle waves, and other complex waveform shapes including noise; (b) A controller, which can include audio power amplifiers and digital signal processing, for operating the apparatus and controlling the frequencies, waveform shapes, amplitudes and phases of specific frequencies, amplitudes and phases of specific waveform components, and overall waveform amplitude and phase, of the one or more HDVE Inertial Drivers; (c) A housing and mounting system; (d) A communication link; and (e) A power source.

In one or more embodiments, an apparatus is adapted to provide selected and variable waveforms to induce shear waves in all, or in one or more portions, of a body (wherein a body can also be an object or a body) for use in elastography and viscoelastography measurement or imaging, comprising: (a) A means of vibration, defined as one or more independent HDVE Inertial Drivers with coupling transfer systems, for producing vibrations of selected frequencies and amplitudes as well as arbitrary complex waveforms such as sine waves, square waves, triangle waves, and other complex waveform shapes including noise; (b) A controlling means, which can include audio power amplifiers and digital signal processing, for operating the apparatus and controlling the frequencies, waveform shapes, amplitudes and phases of specific frequencies, amplitudes and phases of specific waveform components, and overall waveform amplitude and phase, of said vibration means; (c) A housing and mounting means for said vibration means selected from the group consisting of: (i) A housing and mounting means in the form of a strap-on harness that conforms to or is conformable to the body or one or more portions of the body to conduct the vibrations to said body or one or more portions of the body (by harness, we mean belt, sash, wrap, sleeve, legging, girdle, corset, garment, vest or other flexible material that conforms to or is conformable to the body or one or more portions of the body); (ii) A housing and mounting means in the form of a table with mounted vibration means; (iii) A housing and mounting means in the form of a movable arm or rail for placing the vibration means into contact with the body or one or more portions of the body; (iv) A housing and mounting means in the form of a portable or nonportable mat with mounted vibration means, said portable mat being able to be placed onto a table or other structure, on which the body or one or more portions of the body are placed, and said nonportable mat being placed on a patient surface permanently or semi-permanently; (v) A housing and mounting means whereby two vibration means are attached or embedded, one on either side, of an ultrasound transducer array or probe; (vi) A housing and mounting means in the form of a combination of the above (such as a table with a movable arm or rail or harness or mat, or other combination); (d) A communication means for connecting said controlling means to said vibration means selected from the group consisting of: (i) wired communication means for connecting said controlling means to said vibration means; (ii) wireless communication means for connecting said controlling means to said vibration means; (iii) A combination of wired and wireless communications means for connecting said controlling means to said vibration means; and (e) A means of powering said controlling means (which in turn powers said vibration means) which could be a standard electric power source such as a battery or AC wall outlet or other source, or a combination thereof for different components in the controlling means.

In one or more embodiments, a means of creating Reverberant, Crawling Wave, or other shear wave fields in deep tissue with a broad frequency range is provided. In one or more embodiments, the means comprises: (a) a plurality of sources; (b) alternatively, an extended source created by incorporating communicating members such as but not limited to a flexible element to one or two discrete sources; (c) sources containing specially designed communicating members such as but not limited to a contact surface dome to communicate with the surface near the area of interest for elastography; (d) applying at least 0.1 pound of contact force to the surface of the body or material by means of an adjustable and flexible contacting apparatus; (e) applying the contact force in a rapid and ergonomic manner to shorten the examination time and the work required by the clinician; (f) creating a Reverberant, Crawling Wave, or other shear wave field in deep tissue with frequencies ranging from 0.1 Hz to 80 kHz frequency and with enough power to cause from 0.1 micrometers to 50 micrometers in tissue displacement to enable processing.

In one or more embodiments, a method is provided whereby patient or material is scanned using HDVE Inertial Driver system, comprised of one or more of the following steps: (a) Clinician or technician identifies general area to be scanned; (b) Clinician or technician determines appropriate HDVE Inertial Driver system(s) for the application; (c) Clinician or technician places appropriate HDVE Inertial Driver system(s) around, on, under, over, and/or near general area to be scanned, and/or places appropriate HDVE Inertial Driver system(s) on surface such as ground, platform, bed, chair, etc. upon which patient or material is then placed; (d) Clinician or technician adjusts positioning of HDVE Inertial Drivers (including patient contact domes and/or other communicating members and flexible members if needed) against patient or material; (e) Clinician or technician initiates appropriate vibration waveforms signal flow as appropriate for the tissue or material being scanned; (f) Signal then flows through processing including but not limited to DSP, EQ, filtering, phase shifting, and pathway distribution; (g) Signal then flows to power amplifier(s), such as but not limited to audio amplifier(s)) and/or inverter(s); (h) Signal then flows to HDVE Inertial Drivers, which transduces electrical signal into physical vibration in patient or material through one or more communicating members; and (i) Clinician or technician scans patient or object and processes the data to create images and/or measurements.

By virtue of the foregoing, it should be appreciated that each device can be used for various elastography and viscoelastography methods including medical imaging, material imaging, nondestructive testing and seismic mapping.

It must be noted that, as used in this specification and the appended claims, the singular forms “a,” “an” and “the” include plural referents unless the content clearly dictates otherwise. Thus, for example, reference to an “acoustic actuator” includes two or more such actuators.

Unless defined otherwise, all technical and scientific terms used herein have the same meaning as commonly understood by one of ordinary skill in the art to which the invention pertains.

It should be noted that, when employed in the present disclosure, the terms “comprises,” “comprising,” and other derivatives from the root term “comprise” are intended to be open-ended terms that specify the presence of any stated features, elements, integers, steps, or components, and are not intended to preclude the presence or addition of one or more other features, elements, integers, steps, components, or groups thereof.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

The invention claimed is:

1. An inertial-driver apparatus for viscoelastographic imaging of a target object, comprising:

(a) two or more inertial driver devices, each device including: (i) a driver interface configured to receive a driver signal from a controller, (ii) a resonating surface that is acoustically transmissive, and (iii) an inertial driver mechanically coupled to the resonating surface to independently generate a resonating displacement thereof; and (b) a support member configured to position the resonating surfaces in acoustically transmissive contact with a surface of the target object while vibrationally isolating the inertial driver devices from structures other than the target object;

wherein the target object includes a viscoelastic material;

wherein the controller generates an independent driver signal for each inertial driver device within an acoustic frequency range between 200 Hz and 80 KHz; and wherein at a driving frequency between 200 Hz and 80 KHz, the apparatus is capable of simultaneously producing: (i) shear-wave tissue displacements between 0.1 and 50 μm and (ii) shear-wave penetration of at least 14 cm in human liver or at least 5 cm in human breast tissue.

2. The inertial driver apparatus of claim 1, wherein the resonating displacement of the resonating surface is oriented along an axis perpendicular to the surface of the target object;

wherein the resonating displacement generates longitudinal vibrations along the axis perpendicular to the surface of the target object; and wherein the longitudinal vibrations of the inertial driver devices project into the target object to produce the shear waves.

3. The inertial driver apparatus of claim 1, wherein the shear waves comprise a shear wave field selected from one of: (i) crawling waves; (ii) reverberant waves; (iii) monodirectional waves; and (iv) arbitrary waves.

4. The inertial driver apparatus of claim 1, further comprising:

an acoustic sensor; and an acoustic frequency analyzer communicatively coupled to the acoustic sensor wherein the acoustic sensor and frequency analyzer are configured to monitor shear waves in the target object up to a scan penetration depth of the acoustic sensor.

5. The inertial driver apparatus of claim 1, wherein the controller generates the independent driver signals with power sufficient to produce the shear waves having an upper frequency of up to 3,000 Hz in in vivo human liver or up to 5,000 Hz in in vivo human breast tissue within the area of interest at depths up to 14 cm in in vivo human liver or at depths up to 5 cm in in vivo human breast tissue with tissue displacements in a range of 0.1 to 50 micrometers (μm).

6. The inertial driver apparatus of claim 4, wherein the controller generates driver signals comprising multiple frequencies to produce shear waves having multiple frequencies for measuring elasticity and viscosity of the viscoelastic material within the area of interest by the acoustic sensor and frequency analyzer.

7. The inertial driver apparatus of claim 1, wherein at least one resonating surface is a loudspeaker encompassed by a housing having a contact surface that contacts the target object and seals an air column separating the resonating surface from the surface of the target object, and the distance separating the resonating surface from the surface of the target object is less than 1 cm, and wherein no acoustic sensor is disposed between the apex of the loudspeaker and the surface of the target object.

8. The inertial driver apparatus of claim 1, wherein at least one resonating surface comprises a resilient surface that conforms to the surface of the target object.

9. The inertial driver apparatus of claim 1, wherein the driver device support member further comprises a compression member that enables the resonating surface to conform to the surface of the target object.

10. The inertial driver apparatus of claim 4, wherein the support member attaches the two or more inertial driver devices in spaced linear alignment on opposing sides of the acoustic sensor wherein the inertial driver apparatus further comprises at least one material selected from the group consisting of elastic materials, viscoelastic materials, and combinations thereof positioned between the inertial driver devices and the acoustic sensor to vibrationally isolate the acoustic sensor from the inertial driver devices while not materially attenuating the displacements of the resonating surfaces of the inertial driver devices.

11. The inertial driver apparatus of claim 1, wherein the support member further comprises an adjustable harness that encircles the target object.

12. The inertial driver apparatus of claim 1, further comprising a flexible substrate upon which the target object is placed wherein the flexible substrate supports the target object and includes apertures through which inertial driver devices contact the target object, wherein the inertial driver devices are not in acoustic communication with the flexible substrate such that the flexible substrate does not materially attenuate the displacements that enter the target object.

13. The inertial driver apparatus of claim 1, wherein the support member comprises a pair of opposing clamp devices configured to position and hold the two or more driver devices against the target object from opposite sides of the target object.

14. The inertial driver apparatus of claim 13, wherein at least one of the pair of opposing clamp devices comprise an engaging member slidingly received in an elongate channel of a table for sliding and locking the position of the at least one of the pair of opposing clamp devices.

15. The inertial driver apparatus of claim 1, wherein the support member comprises a base that can be placed upon a table structure and a plurality of spring members.

16. The inertial driver apparatus of claim 15, wherein the two or more inertial driver devices are independently driven and each of the resonating surfaces form an adjacent portion of a unitary surface and are joined together with a flexible material that vibrationally isolates each resonating surface from the other resonating surfaces within the unitary surface, wherein the independent acoustic vibrations from each of the resonating surfaces vibrates at substantially the same frequency content and phase as the respective driver signal, and wherein the unitary surface is fluid-impermeable.

17. An elastographic and viscoelastographic imaging system comprising:

(a) a controller;

(b) at least two inertial driver devices, each device including: (i) a driver interface configured to receive a driver signal from the controller, (ii) a resonating surface that is acoustically transmissive, and (iii) an inertial driver mechanically coupled to the resonating surface to independently generate a resonating displacement thereof;

(c) a support member configured to position the resonating surfaces in acoustically transmissive contact with a surface of the target object while vibrationally isolating the inertial driver devices from structures other than the target object;

(d) an imaging device configured to measure tissue displacements within the target object in response to operation of the inertial driver devices; and (e) a processor configured to estimate at least one viscoelastic parameter of the target object based on the measured tissue displacements;

wherein the controller is configured to generate an independent driver signal for each inertial driver device within a frequency range between 200 Hz and 80 KHz; and wherein at a driving frequency between 200 Hz and 80 KHz, the system simultaneously produces (i) shear-wave tissue displacements between 0.1 and 50 micrometers and (ii) shear-wave penetration of at least 14 centimeters in human liver or at least 5 centimeters in human breast tissue.

18. The imaging system of claim 17, wherein the resonating displacement of the resonating surface is oriented along an axis perpendicular to the surface of the target object;

wherein the resonating displacement generates longitudinal vibrations along the axis perpendicular to the surface of the target object; and wherein the longitudinal vibrations project into the target object to produce the shear waves.

19. A method of viscoelastographic imaging of a target object, comprising:

positioning at least two inertial driver devices so that respective resonating surfaces are in acoustically transmissive contact with a surface of the target object while vibrationally isolating the inertial driver devices from structures other than the target object;

generating, by a controller, independent driver signals for the respective inertial driver devices within a frequency range between 200 Hz and 80 KHz; and operating the inertial driver devices to drive the resonating surfaces to independently generate resonating displacement of the target object;

wherein at a driving frequency between 200 Hz and 80 KHz, the operating simultaneously produces (i) shear-wave tissue displacements between 0.1 and 50 micrometers and (ii) shear-wave penetration of at least 14 centimeters in human liver or at least 5 centimeters in human breast tissue;

acquiring displacement data from an imaging device; and estimating at least one viscoelastic parameter of the target object based on the displacement data.

20. The method of claim 19, wherein the resonating displacement of the resonating surface is oriented along an axis perpendicular to the surface of the target object;

wherein the resonating displacement generates longitudinal vibrations along the axis perpendicular to the surface of the target object; and wherein the longitudinal vibrations project into the target object to produce the shear waves.

* * * * *